(12) United States Patent
Prutchi et al.

(10) Patent No.: US 7,027,863 B1
(45) Date of Patent: Apr. 11, 2006

(54) DEVICE FOR CARDIAC THERAPY

(75) Inventors: David Prutchi, Lake Jackson, TX (US); Nissim Darvish, Haifa (IL); Andre G. Routh, Lake Jackson, TX (US); Edward Haluska, Angleton, TX (US); Ziv Belsky, Haifa (IL)

(73) Assignee: Impulse Dynamics N.V., Curacao (AN)

( * ) Notice: Subject to any disclaimer, the term of this patent is extended or adjusted under 35 U.S.C. 154(b) by 246 days.

(21) Appl. No.: 10/111,516

(22) PCT Filed: Oct. 25, 2000

(86) PCT No.: PCT/IL00/00682

§ 371 (c)(1),
(2), (4) Date: Oct. 21, 2002

(87) PCT Pub. No.: WO01/30436

PCT Pub. Date: May 3, 2001

Related U.S. Application Data

(63) Continuation of application No. PCT/IL00/00682, filed on Oct. 25, 2000.

(60) Provisional application No. 60/161,328, filed on Oct. 25, 1999, provisional application No. 60/161,899, filed on Oct. 27, 1999, provisional application No. 60/161,900, filed on Oct. 27, 1999.

(51) Int. Cl.
*A61N 1/39* (2006.01)

(52) U.S. Cl. .......................................................... 607/5
(58) Field of Classification Search ................ 607/4–14
See application file for complete search history.

(56) References Cited

U.S. PATENT DOCUMENTS 3,572,345 A    3/1971    Auphan (Continued)

FOREIGN PATENT DOCUMENTS

EP    148687    7/1985

(Continued)

OTHER PUBLICATIONS

Dennis A. Brumwell et al "The Amplifier: Sensing the Depolarization", Implantable Cardioverter Defibrillator Therapy: The Engineering-Clinical Interface, Chapter 14, pp. 275-302, EDS. Mark W. Kroll and Michael H. Lehmann, Kluwer Academic Publishers, USA, 1997.

(Continued)

*Primary Examiner*—Scott M. Getzow
(74) *Attorney, Agent, or Firm*—Wolf, Block, Schorr & Solis-Cohen LLP; William H. Dippert

(57) ABSTRACT

A multi-modal cardiotherapy device (100) includes an anti-arrhythmic unit (118) for delivering multiple types of anti-arrhythmic therapy to a heart, a cardiac contractility modulating unit (108) for delivering cardiac contractility modulating signals to the heart, and for applying anti-arrhythmic cardiac contractility modulating signal therapy to the heart, one or more sensing units (112) for sensing electrical signals related to electrical activity of the heart to provide an output signal, one or more detecting units (116) operatively connected to the sensing unit(s) (112) for detecting in the output signal cardiac events of the heart, a controller unit (106) operatively connected to the anti-arrhythmic unit (118), the cardiac contractility modulating unit (108) and the detecting unit(s) (116). The controller unit (106) processes the output of the detecting unit(s) (116) to detect a cardiac arrhythmia or indications of a possible arrhythmia in the heart and controls the application of anti-arrhythmic therapy, anti-arrhythmic cardiac contractility modulating signal therapy, and cardiac contractility modulating therapy to the heart. The device may be an implantable device or a non-implantable device. The device (100) may also include a pacing unit (102). Methods are disclosed for using the device for delivering multi-modal cardiotherapy to the heart.

44 Claims, 8 Drawing Sheets

U.S. PATENT DOCUMENTS

| | | |
|---|---|---|
| 3,587,567 A | 6/1971 | Schiff |
| 3,651,805 A | 3/1972 | Breiling |
| 3,942,536 A | 3/1976 | Mirowski et al. |
| 3,952,750 A | 4/1976 | Mirowski et al. |
| 4,030,509 A | 6/1977 | Heilman et al. |
| 4,106,494 A | 8/1978 | McEachern |
| 4,164,216 A | 8/1979 | Person |
| 4,184,493 A | 1/1980 | Langer et al. |
| 4,202,340 A | 5/1980 | Langer et al. |
| 4,223,678 A | 9/1980 | Langer et al. |
| 4,237,895 A | 12/1980 | Johnson |
| 4,273,114 A | 6/1981 | Barkalow et al. |
| 4,312,354 A | 1/1982 | Walters |
| 4,316,472 A | 2/1982 | Mirowski et al. |
| 4,384,585 A | 5/1983 | Zipes |
| 4,387,717 A | 6/1983 | Brownlee et al. |
| 4,403,614 A | 9/1983 | Engle et al. |
| 4,407,288 A | 10/1983 | Langer et al. |
| 4,440,172 A | 4/1984 | Langer |
| 4,506,680 A | 3/1985 | Stokes |
| 4,543,738 A | 10/1985 | Mower |
| 4,543,956 A | 10/1985 | Herscovici |
| 4,554,922 A | 11/1985 | Prystowsky et al. |
| 4,559,946 A | 12/1985 | Mower |
| 4,559,947 A | 12/1985 | Renger et al. |
| 4,566,456 A | 1/1986 | Koning |
| 4,572,191 A | 2/1986 | Mirowski et al. |
| 4,628,934 A | 12/1986 | Pohndorf et al. |
| 4,651,716 A | 3/1987 | Forester |
| 4,674,508 A | 6/1987 | DeCote |
| 4,679,572 A | 7/1987 | Baker, Jr. |
| 4,690,155 A | 9/1987 | Hess |
| 4,726,379 A | 2/1988 | Altman et al. |
| 4,765,341 A | 8/1988 | Mower et al. |
| 4,830,006 A | 5/1989 | Haluska et al. |
| 4,928,688 A | 5/1990 | Mower |
| 4,971,058 A | 11/1990 | Pless et al. |
| 4,979,507 A | 12/1990 | Heinz et al. |
| 4,998,531 A | 3/1991 | Bocchi et al. |
| 5,003,976 A | 4/1991 | Alt |
| 5,020,544 A | 6/1991 | Dahl et al. |
| 5,022,396 A | 6/1991 | Watanabe |
| 5,044,375 A | 9/1991 | Bach, Jr. et al. |
| 5,083,564 A | 1/1992 | Scherlag |
| 5,087,243 A | 2/1992 | Avitall |
| 5,097,832 A | 3/1992 | Buchanan |
| 5,111,815 A | 5/1992 | Mower |
| 5,129,394 A | 7/1992 | Mehra |
| 5,137,021 A | 8/1992 | Wayne et al. |
| 5,154,501 A | 10/1992 | Svenson et al. |
| 5,156,147 A | 10/1992 | Warren et al. |
| 5,156,149 A | 10/1992 | Hudrlik |
| 5,161,527 A | 11/1992 | Nappholz |
| 5,163,428 A | 11/1992 | Pless |
| 5,172,699 A | 12/1992 | Svenson et al. |
| 5,184,620 A | 2/1993 | Cudahy et al. |
| 5,199,428 A | 4/1993 | Obel et al. |
| 5,205,284 A | 4/1993 | Freeman |
| 5,213,098 A | 5/1993 | Bennett et al. |
| 5,236,413 A | 8/1993 | Feiring |
| 5,281,219 A | 1/1994 | Kallok |
| 5,282,785 A | 2/1994 | Shapland et al. |
| 5,284,491 A | 2/1994 | Sutton et al. |
| 5,286,254 A | 2/1994 | Shapland et al. |
| 5,305,745 A | 4/1994 | Zacouto |
| 5,320,642 A | 6/1994 | Scherlag |
| 5,320,643 A | 6/1994 | Roline et al. |
| 5,327,887 A | 7/1994 | Nowakowski |
| 5,346,506 A | 9/1994 | Mower et al. |
| 5,353,800 A | 10/1994 | Pohndorf |
| 5,366,486 A | 11/1994 | Zipes et al. |
| 5,368,040 A | 11/1994 | Carney |
| 5,370,665 A | 12/1994 | Hudrlik |
| 5,386,837 A | 2/1995 | Sterzer |
| 5,387,419 A | 2/1995 | Levy |
| 5,391,192 A | 2/1995 | Lu |
| 5,391,199 A | 2/1995 | Ben-Haim |
| 5,398,683 A | 3/1995 | Edwards |
| 5,415,629 A | 5/1995 | Henley |
| 5,417,717 A | 5/1995 | Salo et al. |
| 5,419,763 A | 5/1995 | Hildebrand |
| 5,425,363 A | 6/1995 | Wang |
| 5,443,485 A | 8/1995 | Housworth |
| 5,443,489 A | 8/1995 | Ben-Haim |
| 5,447,520 A | 9/1995 | Spano |
| 5,458,568 A | 10/1995 | Racchini et al. |
| 5,464,020 A | 11/1995 | Lerner |
| 5,468,254 A | 11/1995 | Hahn |
| 5,472,453 A | 12/1995 | Alt |
| 5,476,484 A | 12/1995 | Hedberg |
| 5,476,485 A | 12/1995 | Weinberg et al. |
| 5,476,497 A | 12/1995 | Mower |
| 5,482,052 A | 1/1996 | Lerner |
| 5,499,971 A | 3/1996 | Shapland et al. |
| 5,501,662 A | 3/1996 | Hofman |
| 5,514,162 A | 5/1996 | Bornzin et al. |
| 5,520,642 A | 5/1996 | Bigagli et al. |
| 5,531,764 A | 7/1996 | Adams et al. |
| 5,540,722 A | 7/1996 | Clare |
| 5,549,646 A | 8/1996 | Katz et al. |
| 5,556,421 A | 9/1996 | Prutchi |
| 5,568,809 A | 10/1996 | Ben-haim |
| 5,571,143 A | 11/1996 | Hoegnelid et al. |
| 5,584,803 A | 12/1996 | Stevens |
| 5,584,868 A | 12/1996 | Salo et al. |
| 5,587,200 A | 12/1996 | Lorenz |
| 5,601,609 A | 2/1997 | Duncan |
| 5,601,611 A | 2/1997 | Fayram et al. |
| 5,626,622 A | 5/1997 | Cooper |
| 5,634,899 A | 6/1997 | Shapland et al. |
| 5,649,966 A | 7/1997 | Noren et al. |
| 5,651,378 A | 7/1997 | Matheny |
| 5,662,687 A | 9/1997 | Hedberg et al. |
| 5,674,251 A | 10/1997 | Combs et al. |
| 5,674,259 A | 10/1997 | Gray |
| 5,683,431 A | 11/1997 | Wang |
| 5,687,734 A | 11/1997 | Dempsey et al. |
| 5,713,935 A | 2/1998 | Prutchi et al. |
| 5,720,768 A | 2/1998 | Verboven-Nelissen |
| 5,735,876 A | 4/1998 | Kroll et al. |
| 5,738,096 A | 4/1998 | Ben-Haim |
| 5,738,105 A | 4/1998 | Kroll |
| 5,749,906 A | 5/1998 | Kieval et al. |
| 5,755,740 A | 5/1998 | Nappholz |
| 5,782,876 A | 7/1998 | Flammang |
| 5,782,881 A | 7/1998 | Lu et al. |
| 5,792,198 A | 8/1998 | Nappholz |
| 5,792,208 A | 8/1998 | Gray |
| 5,797,967 A | 8/1998 | KenKnight |
| 5,800,464 A | 9/1998 | Kieval |
| 5,807,234 A | 9/1998 | Bui et al. |
| 5,807,306 A | 9/1998 | Shapland et al. |
| 5,814,079 A | 9/1998 | Kieval |
| 5,865,787 A | 2/1999 | Shapland et al. |
| 5,871,506 A | 2/1999 | Mower |
| 5,906,607 A | 5/1999 | Taylor et al. |
| 5,913,876 A | 6/1999 | Taylor et al. |
| 5,927,284 A | 7/1999 | Borst et al. |
| 6,032,074 A | 2/2000 | Collins |
| 6,032,672 A | 3/2000 | Taylor |
| 6,041,252 A | 3/2000 | Walker et al. |
| 6,067,470 A | 5/2000 | Mower |
| 6,071,305 A | 6/2000 | Brown et al. |
| 6,086,582 A | 7/2000 | Altman et al. |

| | | |
|---|---|---|
| 6,136,019 A | 10/2000 | Mower |
| 6,141,586 A | 10/2000 | Mower |
| 6,144,880 A | 11/2000 | Ding et al. |
| 6,151,586 A | 11/2000 | Brown |
| 6,152,882 A | 11/2000 | Prutchi |
| 6,178,351 B1 | 1/2001 | Mower |
| 6,223,072 B1 | 4/2001 | Mika et al. |
| 6,233,487 B1 | 5/2001 | Mika et al. |
| 6,263,242 B1 | 7/2001 | Mika et al. |
| 6,263,460 B1 | 7/2001 | Spilo et al. |
| 6,295,470 B1 | 9/2001 | Mower |
| 6,337,995 B1 | 1/2002 | Mower |
| 6,341,235 B1 | 1/2002 | Mower |
| 6,343,232 B1 | 1/2002 | Mower |
| 6,360,123 B1 | 3/2002 | Kimchi et al. |
| 6,360,126 B1 | 3/2002 | Mika et al. |
| 6,370,430 B1 | 4/2002 | Mika et al. |
| 6,411,847 B1 | 6/2002 | Mower |
| 6,424,866 B1 | 7/2002 | Mika et al. |
| 6,459,928 B1 | 10/2002 | Mika et al. |
| RE38,119 E | 5/2003 | Mower |

FOREIGN PATENT DOCUMENTS

| | | |
|---|---|---|
| EP | 0314078 A1 | 5/1989 |
| JP | 04117967 A2 | 4/1992 |
| JP | 4365493 | 12/1992 |
| JP | 7126600 | 5/1995 |
| JP | 8243176 A2 | 9/1996 |
| WO | WO 92/00716 | 1/1992 |
| WO | WO 95/08316 | 9/1995 |
| WO | WO 97/25101 | 1/1997 |
| WO | WO97/25098 | 7/1997 |
| WO | WO98/10828 | 3/1998 |
| WO | WO98/10829 | 3/1998 |
| WO | WO98/10830 | 3/1998 |
| WO | WO98/10831 | 3/1998 |
| WO | WO98/10832 | 3/1998 |
| WO | WO01/30139 | 5/2001 |
| WO | WO01/30445 | 5/2001 |
| WO | WO 200004947 | 1/2002 |

OTHER PUBLICATIONS

C.G. Supino, "The System", Implantable Cardioverter Defibrillator Therapy: The Engineering-Clinical Interface, Chapter 8, pp. 163-172, EDS. Mark W. Kroll and Michael H. Lehmann, Kluwer Academic Publishers, USA, 1997.

Stan M. Bach, Tachyarrhythmia Detection, Implantable Cardioverter Defibrillator Therapy: The Engineering-Clinical Interface, Chapter 15, pp. 303-323, EDS. Mark W. Kroll and Michael H. Lehmann, Kluwer Academic Publishers, USA, 1997.

Michael L. Hardage and Michael B. Sweeney, "Anti-Tachycardia Pacing and Cardioversion", Implantable Cardioverter Defibrillator Therapy: The Engineering-Clinical Interface, Chapter 16, pp. 325-342, EDS. Mark W. Kroll and Michael H. Lehmann, Kluwer Academic Publishers, USA, 1997.

Verrier et al., "Electrophysiologic Basis for T Wave Alternans as an Index of Vulnerability to Ventricular Fibrillation", Journal of Cardiovascular Electrophysiology, vol. 5, pp. 445-461, 1994.

H. Antoni et al., "Polarization Effects of Sinusoidal 50-Cycle Alternating Current on Membrane Potential of Mammalian Cardiac Fibres", Pflugers Arch. 314, pp. 274-291, 1970.

Antman, E.M. et al. "Treatment of 150 Cases of Life-Threatening Digitalis Intoxication with Digoxin-Specific Fab Antibody Fragments;" Jun. 1990 Circulation; vol. 81: No. 6: pp. 1744-1752.

Bakker, P.F., et al., "Beneficial Effects of Biventricular Pacing of Congestive Heart Failure", PACE, vol. 17, Apr. 1994, Part 11, one page.

Bakker, P.F., et al., "Biventricular Pacing Improves Functional Capacity in Patients with End-Stage Congestive Heart Failure" PACE, vol. 17, Apr. 1995, Part 11, one page.

Bargheer K. et al., "Prolongation of Monophasic Action Potential Duration and the Refractory Period in the Human Heart by Tedisamil, a New Potassium-Blocking Agent", J. Eur Heart 15 (10), Oct. 1994. pp. 1409-1414.

Bers, D.M., Excitation-Contraction Coupling and Cardiac Contractile Force, Kluwer Academic Publishers, London, 1993.

Borst, et al. "Coronary Artery Bypass Without Cardiopulmonary and Without Interuption of Native Coronary Flow Using a Novel Anastomosis site restraining device ('Ocyupus')", Journal of the American College of Cardiology, 27 (6), May 1996.

Cano, N.J. et al. "Dose-Dependent Reversal of Digoxin-Inhibited Activity of an In-Vitro NA+K+ATPase Model by Digoxin-Specific Antibody;" May 1996; pp. 107-1011; Toxicology Letters; vol, 85; No.2.

Cazeau S. et al., "Multisite Pacing for End-Stage Heart Failure: Early Experience", Pacing and Clinical Electrophysiology vol. 19, Nov. 1996, Part 11, pp. 1748-1757.

Cooper, W., "Postextrasystolic Potentiation: Do We Really Know What It Means and How to Use It?" Circulation, vol. 88, No. 6, Dec. 1993, pp. 2962-2971.

Dillon, SM., "Optical Recordings in the Rabbit Heart Show that Defibrillation Strength Shocks Prolong the Duration of Depolarization and the Refractory Period" in Circ Res., 69(3), Sep. 1991, pp. 842-856.

Dillon, SM., abstract of "Synchronized Repolarization After Defibrillation Shocks. A Possible Component of the Defibrillation Process Demonstration By Optical Recordings in Rabbit Heart", Circulation, May 1992, vol. 85, No. 5, pp. 1865-1878.

Fain, E.S., et al. "Improved Internal Defibrillation Efficacy with Biphasic Waveform", American Heart Journal 117 (2), Feb. 1989, pp. 358-364.

Fleg, J.L. et al., "Impact of Age on the Cardiovascular Response to Dynamic Upright Exercise in Healthy Men and Women", J. Appl. Physiol., vol. 78, 1995, p. 890.

Foster, A.H. et al., "Acute Hemodynamic Effects of Atrio-Biventricular Pacing in Humans", 1995. The Society of Thoracic Surgeons vol. 59, pp. 294-299.

Franz, M.R., "Bridging the Gap Between Basic and Clinical Electrophysiology: What Can be Learned from Monophasic Action Potential Recording?", J. Cardiovasc Electrophysiol 5(8), Aug. 1994. pp. 699-710.

Franz, M.R., "Method and Theory of Monophasic Action Potential Recording", Prog. Cardiovasc Dis 33 (6), May-Jun. 1991, pp. 347-368.

Franz, M.R., "Progress in Cardiovascular Disease: Monophasic Action Potential Symposium, I. Introduction", Prog. Cardiovasc Dis 33 (6), May-Jun. 1991 pp. 345-346.

Fromer et al., "Ultrarapid Subthreshold Stimulation for Termination of Atrioventricular Node Reentrant Tachycardia", Journal of the American College of Cardiology 20 (Oct. 1992), pp. 879-883.

Fu. P and B.J. Bardakjian, "System Identification of Electrically Coupled Smooth Muscle Cells: The Passive Electrically Coupled Smooth Muscle Cells: The Passive Electrical Properties", published in IEEE Transactions on Biomedical Engineering, 38(11), pp. 1130-1140, 1991.

Ham, Frederic M and Han, Soowhan, "Classification of Cardiac Arrhythmias Using Fuzzy Artmap": IEEE Transactions on Biomedical Engineering, vol. 43, No. 4, Apr. 1996.

Hoffman, B.F. et al., "Effects of Postextrasystolic Potentiation on Normal & Failing Hearts", Bulletin of New York Academy of Medicine, 41 in 1965, pp. 498-534.

Josephson, M.E., Clinical Cardiac Electrophysiology: Techniques and Interpretations, 2nd. Edition, Lea & Febiger, Philadelphia, 1991.

King, A. et al., The Inotropic Action of Paired Pulse Stimulation in the Normal and Failing Heart: An Experimental Study, Cardiovascular Research, vol. 2, Apr. 1968, pp. 122-129.

Knisley et al., "Prolgongation and Shortening of Action Potentials by Electrical Shocks in Frog Ventricular Muscle", American Journal of Physiology 6 (Heart Circ. Physiol. 35, 1994) pp. H2348-H2358.

Koller, et al., "Relation Between Repolarization and Refractoriness During Programmed Electrical Stimulation in the Human Right Ventricle", Circulation 91(9), 2378-2384, 1995.

Langberg, Jonathan J. et al., "Identification of Ventricular Tachycardia with Use of the Morphology of the Endocardial Electrogram", Circulation, vol. 77, No. 6, Jun. 1988.

McVeigh, E.R et al., "Noninvasive Measurement of Transmural Gradients in Myocardial Strain with MR Imaging", Radiology 180 (3), Sep. 1991. pp. 677, 679-684.

Mercando, A.D., et al., "Automated Detection of Tachardies by Antitachicardia Devices", Chapter 100, pp. 943-948, in Cardiac Electrophysiology from Cell to Bedside, Eds. Douglas P. Zipes and Jose Jalife, publishers W.B. Saunders Company (1990).

Moran, R.J. et al; "Digoxin-Specific Fab Fragments Impair Renal Function in the Rat:" 1994; pp. 854-856; Journal of Pharmacy and Pharmacology: vol. 46: No 10.

Morse, et al., "A Guide to Cardiac Pacemakers,Defibrillators and Related Products", Droege Computing Services, Durham, NC.

Merck Manual, The. Section 3, the 16th Edition of the Merck Manual, Published in 1992.

Paul, Ve., et al. "Automatic Recognition of Ventricular Arrythmias Using Temporal Electrogram Analysis" Pace, vol. 14, pp. 1265-1273, (1991).

Qiuzhen Xue et al., "Neural-Network-Based Adaptive Matched Filtering for QRS Detection", IEEE Transactions on Biomedical Engineering. vol. 39. No. 4. Apr. 1992.

Saksena et al., "Dual-site Atrial Pacing in Atrial Fibrillation", JACC, vol. 28, No. 3, Sep. 1996, pp. 687-694.

Shumaik, G.M. et al. "Oleander Poisoning; Treatment with Digoxin-Specific Fab Antibody Fragments;" Jul. 1988; pp. 732-735: Annals of Emergency Medicine: vol. 17: No. 7.

Sweeny RJ, et al., abstract of "Countershock Strength-Duration Relationship for Myocardial Refractory Period Extension", Acad Emerg. Med., Jan. 1995, vol. 2, No. 1, pp. 57-62.

Sweeny RJ. et al., abstract of "Refractory Interval After Transcardiac Shocks During Ventricular Fibrillation", Circulation, Dec. 1996, vol. 94, No. 11, pp. 2947-2952.

Sweeny RJ, et al., abstract of "Ventricular Refractory Period Extension Caused by Defibrillation Shocks", Circulation, Sep. 1990, vol. 82, No. 3, pp. 965-972.

Talit, U. et al., "The Effect of External Cardiac Pacing on Stroke Volume", Pace 13, May 1990, pp. 598-560.

Tsong, T.Y., "Electroportion of Cell Membranes" Aug. 1991; pp. 297-306; Biophysical Journal; vol. 60.

Webster, John G., ed., Design of Carduac Pacemakers, IEEE Press, Piscataway, New Jersey, 1995.

Wessale, J.L. et al., "Stroke Volume and Three Phase Cardiac Output Rate Relationship with Ventricular Pacing" Pace 13, May 1990. pp. 673-680.

Wirtzfeld, A. et al., "Physiological Pacing: Present Status and Future Developments", Pace 10 Jan.-Feb. 1987, Part I, pp. 41-57.

Zipes. D et al., Cardiac Electrophysiology from Cell to Bedside, 1990, W.B. Saunders Co., Philadelphia.

Guidant Product Catalogue, 2001, 2 pages.

"The Latest Tetralogy of Fallot Discussion with Graphical Support Including Video of Echocardiography and Catherization" Pediatric Electrophysiologypicu Book ("An On-Line Resource for Pediatric Critical Care").

Brumwell D.A. et al. "The Amplifier: Sensing the Depolarization", Implantable Cardioverter Defibrillator Therapy: The Engineering-Clinical Interface, Chapt. 14, pp. 275-302. Eds. Kroll and Lehmann, Kluwer Academic Publishers, USA 1997.

Gill RJ. et al., abstract of "Refractory Period Extension During Ventricular Pacing at Fibrillatory Pacing Rates" Pacing Clin. Elctrophysiol, Mar. 1997, vol. 20. No. 3, pp. 647-653.

Hardage, M.l. and Sweeney, M.B., "Anti-Tachycardia Pacing and Cardioversion", Implantable Cardioverter Defibrillator Therapy: The Engineering-Clinical Interface, Chapt. 6, pp. 325-342. Eds. Mark W. Kroll and Michael H. Lehmann. Kluwer Academic Publishers U.S.A 1997.

Matheny R.G. and C.J. Shear, "Vagus Nerve Stimulation as a Method to Temporarily Slow or Arrest the Heart" Annals of Thoracic Surgery. 63 (6) Supplement, pp. S28-29, Jun. 1997.

Supino, C.G. "The Systems", Implantable Cardioverter Defibrillator Therapy: The Engineering-Clinical Interface, Chapt. 8, pp. 163-172, Eds. Mark W. Kroll and Michael H. Lehmann, Kluwer Academic Publishers, USA 1997.

Thakor et al., "Effect of Varying Pacing Waveform Shapes on Propagation and Hemodynamics in the Rabbit Heart", The American Journal of Cardiology 79 (6A), pp. 36-43, 1997.

DEVICE FOR CARDIAC THERAPY

CROSS REFERENCES TO RELATED APPLICATIONS

This patent application is related to and claims priority from commonly owned U.S. Provisional Patent applications Ser. No. 60/161,328, filed Oct. 25, 1999 entitled "CARDIAC CONTRACTILITY MODULATION DEVICE HAVING ANTI-ARRHYTHMIC CAPABILITIES AND A METHOD OF OPERATING THEREOF", Ser. No. 60/161,899 filed Oct. 27, 1999 entitled "DEVICE FOR CARDIAC THERAPY", and Ser. No. 60/161,900 filed Oct. 27, 1999 entitled "ANTI-ARRHYTHMIC DEVICE AND A METHOD OF DELIVERING ANTI-ARRHYTHMIC CARDIAC THERAPY", all three Provisional Patent Applications are incorporated herein by reference in their entirety.

FIELD OF THE INVENTION

The present invention relates generally to the field of cardiotherapy devices and more particularly to cardio-therapeutic devices having cardiac contractility modulation capabilities and including multi-modal anti-arrhythmic therapy capabilities.

BACKGROUND OF THE INVENTION

Anti-arrhythmic cardiac devices are well known in the art. Such devices include implantable and non-implantable devices which are used for detecting various types of arrhythmic conditions in a cardiac patient and for applying an appropriate anti-arrhythmic therapy to the heart.

For example, various pacemaker devices may detect various types of brady-arrhythmias (also known as bradycardias) and provide artificial pacing therapy to one or more cardiac chambers.

Other types of anti-arrhythmic devices such as cardiac defibrillators, and other anti-tachyarrhythmia devices such as defibrillator/cardioverter devices are designed to detect various different types of tachy-arrhythmias (also known as tachycardias) such as ventricular tachycardia (VT) which is a non-fibrillation type of tachy-arrhythmia and ventricular fibrillation (VF), and to provide one or more types of appropriate anti-tachycardia therapy to the heart such as anti-tachycardia pacing (ATP) therapy, cardioverting shock therapy and shock defibrillation therapy. Such devices may use multi-tiered tachy-arrhythmia detection algorithms (also known as classification algorithms) for distinguishing between VT, VF and supra-ventricular tachycardia (SVT) arising from atrial fibrillation and for applying the proper type of therapy selected from ATP therapy, low or medium energy cardioversion shock therapy, and high energy defibrillating shock therapy.

U.S. Pat. No. 4,403,614 to Engle et al titled "IMPLANTABLE CARDIOVERTER", incorporated herein by reference, discloses an implantable cardioverter/defibrillator device capable of delivering cardioversion therapy pulses having an energy level lower than necessary for defibrillation as well as defibrillating pulses.

Some modern implantable Cardiotherapy devices are adapted to include a combination of various cardiac therapeutic modes. For example, implantable cardio-therapy devices may use a combination of anti-bradycardia pacing, ATP pacing, cardioversion and automatic defibrillating shock therapy. U.S. Pat. No. 4,830,006 to Haluska et al. titled "IMPLANTABLE CARDIAC STIMULATOR FOR DETECTION AND TREATMENT OF VENTRICULAR ARRHYTHMIAS", incorporate herein by reference, discloses a cardiac stimulator device which integrates the functions of bradycardia and anti-tachycardia pacing therapies and cardioversion and defibrillation shock therapies.

Recently, a new method of cardiotherapy has been introduced for modifying the cardiac contractility by delivering non-excitatory electrical signals to the myocardium at a selected time such that the electrical signals do not result in exciting propagating myocardial action potentials due to myocardial refractoriness. While such non-excitatory electrical signals do not lead to propagating myocardial action potentials, they may modulate the myocardial contractility in naturally or artificially paced cardiac beats.

Devices for performing this contractility modulating cardiotherapy are known as excitable tissue control (ETC) devices, and are also known as cardiac contractility modulation (CCM) devices. It is noted that the terms CCM and ETC are interchangeably used throughout the present application and refer to methods for modulating cardiac contractility by delivering non-excitatory electrical signals to the heart. Similarly, the terms CCM device and ETC device are interchangeably used throughout the present application and refer to devices adapted for modulating cardiac contractility by delivering non-excitatory electrical signals to the heart.

ETC devices modulate the activity of excitable tissues by application of non-excitatory electrical signals to the heart (or other excitable tissues) through suitable electrodes in contact with the tissue. For example, ETC devices may be used, inter alia, to increase or decrease the contractility of cardiac muscle in vitro, in vivo and in situ., as disclosed in detail in PCT application, International Publication Number WO 97/25098 to Ben-Haim et al., titled "ELECTRICAL MUSCLE CONTROLLER", incorporated herein by reference. Other methods and applications of ETC devices are disclosed in PCT applications commonly-assigned to the assignee of the present application, International Publication Number WO 98/10828, titled "APPARATUS AND METHOD FOR CONTROLLING THE CONTRACTILITY OF MUSCLES" to Ben Haim et al., incorporated herein by reference, International Publication Number WO 98/10829, titled "DRUG-DEVICE COMBINATION FOR CONTROLLING THE CONTRACTILITY OF MUSCLES" to Ben Haim et al., incorporated herein by reference and International Publication Number WO 98/10830, titled "FENCING OF CARDIAC MUSCLES" to Ben Haim et al., incorporated herein by reference, International Publications Number WO 98/10831 to Ben Haim et al., titled "CARDIAC OUTPUT CONTROLLER", incorporated herein by reference.

Further applications of the ETC including devices combining cardiac pacing and cardiac contractility modulation are disclosed in PCT Application, International Publication No. WO 98/10832, titled "CARDIAC OUTPUT ENHANCED PACEMAKER" to Ben Haim et al., co-assigned to the assignee of the present application. Such ETC devices function by applying non-excitatory electrical field signals of suitable amplitude and waveform, appropriately timed with respect to the heart's intrinsic electrical activity to selected cardiac regions. The contraction of the selected regions may be modulated to increase or decrease the stroke volume of the heart. The timing of the ETC signals must be carefully controlled since application of the ETC signal to the myocardium at an inappropriate time may be arrhythmogenic. The ETC signals must therefore be applied to the selected cardiac region within a defined time interval during which the selected cardiac region will not be stimulated by the ETC signals.

As disclosed in International Publication No. WO 98/10832, the ETC signals may be timed relative to a trigger signal which is also used as a pacing trigger, or may be timed relative to locally sensed electrogram signals.

Co-pending U.S. patent application to Mika et al., Ser. No. 09/276,460, Titled "APPARATUS AND METHOD FOR TIMING THE DELIVERY OF NON-EXCITATORY ETC SIGNALS TO A HEART", filed Mar. 25, 1999, assigned to the common assignee of the present application, the entire specification of which is incorporated herein by reference, and the corresponding PCT application, International Application No. PCT/IL00/00126, International Publication No. WO 00/57952, disclose a method for timing the delivery of non-excitatory ETC signals to a heart using, inter alia, an alert window period for reducing the probability of delivering an improperly timed ETC signal to the heart due to spurious detection of noise or ectopic beats.

Co-pending U.S. patent application Ser. No. 09/328,068 to Mika et al., titled "APPARATUS AND METHOD FOR COLLECTING DATA USEFUL FOR DETERMINING THE PARAMETERS OF AN ALERT WINDOW FOR TIMING DELIVERY OF ETC SIGNALS TO A HEART UNDER VARYING CARDIAC CONDITIONS", filed Jun. 8, 1999, the entire specification of which is incorporated herein by reference, and the corresponding PCT application, International Application No. PCT/IL00/00310, disclose devices and methods for collecting patient data which is usable for the operation of a device for timing of delivery of ETC signals to the heart using, inter alia, a dynamically varying alert window period for event sensing.

Co-pending U.S. patent application Ser. No. 09/338,649 to Mika et al., titled "APPARATUS AND METHOD FOR SETTING THE PARAMETERS OF AN ALERT WINDOW USED FOR TIMING THE DELIVERY OF ETC SIGNALS TO A HEART UNDER VARYING CARDIAC CONDITIONS", filed Jun. 23, 1999, the entire specification of which is incorporated herein by reference, and the corresponding PCT application, International Application No. PCT/IL00/00321, disclose devices and methods for timing of delivery of ETC signals to the heart using, inter alia, a dynamically varying alert window period for event sensing.

Application of ETC therapy to the heart may enhance the cardiac output without increasing the heart rate. Such therapy may be advantageously applied, inter alia, to patients having no diagnosed cardiac rhythm abnormalities as well as to patients such as congestive heart failure (CHF) patients which are particularly prone to episodes of VT or VF. Since cardiac patients such as, inter alia, CHF patients may benefit from the use of implantable or non-implantable anti-arrhythmic devices, such as defibrillator, Defibrillator/cardioverter devices and the like, it may be advantageous to implement a single device which is capable of delivering anti-arrhythmic therapy and ETC therapy to a cardiac patient. For example, such a device may be capable of delivering ETC therapy and defibrillating shock therapy to a patient, when a need for such therapy is detected.

While the various methods of timing the delivery of ETC signals to the heart disclosed in the above co-pending U.S. patent application Ser. Nos. 09/276,460, 09/328,068 and 09/338,649 to Mika et al., and in the corresponding PCT applications, greatly reduce the probability of inducing arrhythmias due to delivery of ETC signals to the heart at a vulnerable time, it may be desirable to include anti-arrhythmia capabilities in ETC or CCM devices as a safety device in case of occurrence of tachy-arrhythmia episodes such as VT or VF, either due to a delivered ETC signal or spontaneously.

Unfortunately, the delivery of ETC signals to the myocardium may lead to electrical artifact signals sensed by the sense electrodes of the anti-arrhythmic device. Such electrical artifact signals may be erroneously detected by the event detecting circuitry of the anti-arrhythmic device as electrical events representing cardiac activation. Such spurious detection of electrical artifacts induced by ETC signals may adversely affect the detection and/or classification of cardiac tachy-arrhythmias. For example, such spurious event detection may result in classification of a normal heart rate as VT or VF leading to unnecessary and potentially dangerous defibrillating shock therapy being delivered to the heart.

Besides the increased patient risk and patient discomfort caused by such unnecessary delivery of defibrillation shock therapy, such erroneous detection of VF followed by defibrillating shock therapy may lead to unnecessary drain on the battery of the device, thus shortening the useful life in implanted devices. Additionally, in devices capable of delivering cardioversion therapy, spurious event detection caused by ETC induced electrical artifacts may result in unnecessary delivery of cardioversion therapy by the device which has the disadvantage of unnecessary battery drain and which may increase patient risk.

Another problem which may result from delivering of ETC signals to the heart of a patient which is monitored by an anti-arrhythmic device such as, inter alia, a defibrillator/cardioverter device, is the possible interference of ETC induced electrical artifacts with the operation of detection circuitry utilizing automatic gain control (AGC) or automatic threshold control (ATC). AGC methods and ATC methods are well known in the art. For example, AGC and ATC methods are disclosed by Dennis A. Brumwell et al., in Chapter 14 titled "THE AMPLIFIER: SENSING THE DEPOLARIZATION" in the book titled "IMPLANTABLE CARDIOVERTER DEFIBRILLATOR THERAPY: THE ENGINEERING-CLINICAL INTERFACE", pp. 275–302, Eds. Mark W. Kroll and Michael H. Lehmann, Kluwer Academic Publishers, USA, 1997.

ETC signal induced artifacts sensed by the defibrillator amplification circuits may cause an undesirable decrease in the gain of the amplifier circuits in defibrillators using AGC based algorithms which may lead to failure to detect VF signal. ETC signal induced artifacts sensed by the defibrillator amplification circuits may also cause an undesirable increase in the threshold level in defibrillators using ATC based algorithms which may also lead to failure to detect VF signal.

The above described interference problems may be encountered in the operation of a variety of different prior art internal cardiac defibrillator (ICD) devices and automatic internal cardioverter defibrillator (AICD) devices, including tiered therapy devices capable of delivering different types of cardiac therapy such as anti-brady-arrhythmic pacing therapy, anti-arrhythmic cardioversion therapy, anti-arrhythmic defibrillating shock therapy, variable energy shock therapy, anti-tachycardia pacing therapy (ATP) and any combination thereof. In the presence of ETC signals delivered by operating CCM or ETC devices.

SUMMARY OF THE INVENTION

There is therefore provided, in accordance with a preferred embodiment of the present invention, a method for operating a multi-modal cardiotherapy device to deliver multi-modal cardiotherapy to a heart. The method includes the steps of providing a device configured for delivering cardiac contractility modulating signals, and a plurality of anti-arrhythmic therapy modalities to the heart, applying cardiac contractility modulating signals to the heart to modulate the contractility of at least a portion of the heart, detecting an arrhythmia or indications of possible arrhythmia in the heart delivering to the heart an anti-arrhythmic therapy selected from the plurality of anti-arrhythmic therapy modalities based on the type of the arrhythmia or the indications detected in the step of detecting, and coordinating the application of cardiac contractility modulating signals of the step of applying with the delivering of the anti-arrhythmic therapy of the step of delivering.

There is also provided, in accordance with a preferred embodiment of the present invention, a method for operating a multi-modal cardiotherapy device to deliver multi-modal cardiotherapy to a heart, the device is configured for delivering cardiac contractility modulating signals and a plurality of anti-arrhythmic therapy modalities to the heart. The method includes the steps of applying cardiac contractility modulating signals to the heart to modulate the cardiac output of the heart, detecting an arrhythmia or indications of possible arrhythmia in the heart, delivering to the heart an anti-arrhythmic therapy selected from the plurality of anti-arrhythmic therapy modalities based on the type of the arrhythmia or the indications detected in the step of detecting, and coordinating the application of cardiac contractility modulating signals of the step of applying with the delivering of the anti-arrhythmic therapy of the step of delivering.

Furthermore, in accordance with another preferred embodiment of the present invention, the plurality of anti-arrhythmic therapy modalities includes cardiac contractility modulating signal anti-arrhythmic therapy and one or more anti arrhythmic therapy modalities selected from defibrillating shock therapy, cardioverting shock therapy, anti-tachycardia pacing therapy, variable energy shock therapy, anti-bradycardia pacing therapy and any combination thereof.

Furthermore, in accordance with another preferred embodiment of the present invention, the cardiac contractility modulating signal anti-arrhythmic therapy includes delivering one or more of the cardiac contractility modulating signals to the heart for reducing the prevalence of arrhythmic episodes detected in the heart.

Furthermore, in accordance with another preferred embodiment of the present invention, the step of applying cardiac contractility modulating signals to the heart is performed for modulating the cardiac output of the heart.

Furthermore, in accordance with another preferred embodiment of the present invention, the step of coordinating includes the step of terminating the applying of cardiac contractility modulating signals to the heart of the step of applying, prior to or upon the delivering to the heart of the anti-arrhythmic therapy.

Furthermore, in accordance with another preferred embodiment of the present invention, the step of coordinating includes the step of renewing the applying of cardiac contractility modulating signals to the heart after the delivering to the heart of the anti-arrhythmic therapy is terminated.

Furthermore, in accordance with another preferred embodiment of the present invention, the indications of possible arrhythmia include the detection of T-wave alternans in the heart.

Furthermore, in accordance with another preferred embodiment of the present invention, the step of detecting further includes the step of determining the heart rate of the heart and disabling the applying of the cardiac contractility modulating signals to the heart within the duration of a cardiac contractility modulating signal free time period if the heart rate is larger than a first threshold value.

Furthermore, in accordance with another preferred embodiment of the present invention, the step of detecting further includes the step of enabling the applying of the cardiac contractility modulating signals to the heart if no arrhythmia or indications of possible arrhythmia are detected within the duration of the cardiac contractility modulating signal free time period.

There is further provided, in accordance with a preferred embodiment of the present invention, a multi-modal cardiotherapy device. The device includes an anti-arrhythmic unit for delivering anti-arrhythmic therapy to the heart. The device also includes a cardiac contractility modulating unit configured for delivering cardiac contractility modulating signals to the heart for modulating the cardiac contractility of at least a portion of the heart, and for applying anti-arrhythmic cardiac contractility modulating signal therapy to the heart. The device also includes a sensing unit for sensing electrical signals related to electrical activity of the heart to provide an output signal. The device also includes a detecting unit operatively connected to the sensing unit for receiving the output signal of the sensing unit and for detecting in the output signal cardiac events of the heart. The device also includes a controller unit operatively connected to the anti-arrhythmic unit, the cardiac contractility modulating unit and the detecting unit, for processing the output of the detecting unit to detect a cardiac arrhythmia or indications of possible arrhythmia, for controlling the application of the anti-arrhythmic therapy by the anti-arrhythmic unit, and for controlling the application of the anti-arrhythmic cardiac contractility modulating signal therapy, and the modulating of the cardiac contractility of the portion of the heart by the cardiac contractility modulating unit. The device also includes at least one power source for providing power to the anti-arrhythmic therapy unit, the cardiac contractility modulating unit, the sensing unit the detecting unit, and the controller unit.

Furthermore, in accordance with another preferred embodiment of the present invention, the anti-arrhythmic unit is configured for delivering to the heart multiple modes of anti-arrhythmic therapy selected from anti-bradycardia pacing therapy, defibrillating shock therapy, cardioverting shock therapy, anti-tachycardia pacing therapy, variable energy shock therapy, and any combination thereof.

Furthermore, in accordance with another preferred embodiment of the present invention, the controller unit is configured for coordinating the application to the heart of anti-arrhythmic therapy by the anti-arrhythmic unit with the application to the heart of the antiarrhythmic cardiac contractility modulating signal therapy by the cardiac contractility modulating unit.

Furthermore, in accordance with another preferred embodiment of the present invention, the controller unit is configured for coordinating the application to the heart of anti-arrhythmic therapy by the anti-arrhythmic unit with the modulating of the cardiac contractility by the cardiac contractility modulating unit.

Furthermore, in accordance with another preferred embodiment of the present invention, the antiarrhythmic unit includes a pacing unit configured for pacing at least one chamber of the heart.

Furthermore, in accordance with another preferred embodiment of the present invention, the cardiac contractility modulating unit is configured for controllably delivering cardiac contractility modulating signal anti-arrhythmic therapy to the heart by controllably delivering one or more of the cardiac contractility modulating signals to the heart for reducing the prevalence of arrhythmic episodes detected in the heart.

Furthermore, in accordance with another preferred embodiment of the present invention, the cardiac contractility modulating unit is configured for modulating the cardiac output of the heart by delivering the cardiac contractility modulating signals to the heart.

Furthermore, in accordance with another preferred embodiment of the present invention, the controller unit is configured for terminating the applying of cardiac contractility modulating signals to the heart prior to or upon the delivering to the heart of the anti-arrhythmic therapy.

Furthermore, in accordance with another preferred embodiment of the present invention, the controller unit is configured for renewing the applying of cardiac contractility modulating signals to the heart after the delivering to the heart of the anti-arrhythmic therapy is terminated.

Furthermore, in accordance with another preferred embodiment of the present invention, the detecting unit is configured for detecting T-wave alternans in the heart, as an indication of a possible cardiac arrhythmia.

Furthermore, in accordance with another preferred embodiment of the present invention, the device further includes electrodes operatively connected to the anti-arrhythmic unit, the cardiac contractility modulating unit, and the sensing unit, for delivering the anti-arrhythmic therapy to the heart, for applying the cardiac contractility modulating signals to the heart, and for sensing the electrical signals, respectively.

Furthermore, in accordance with another preferred embodiment of the present invention, the controller unit is configured for determining the heart rate of the heart and for disabling the modulating of the cardiac contractility of the portion of the heart by the cardiac contractility modulating unit within the duration of a cardiac contractility modulating signal free time period if the heart rate is larger than a first threshold value.

Furthermore, in accordance with another preferred embodiment of the present invention, the controller unit is configured for enabling the modulating of the cardiac contractility of the portion of the heart by the cardiac contractility modulating unit if no arrhythmia or indications of possible arrhythmia are detected within the duration of the cardiac contractility modulating signal free time period.

There is also provided, in accordance with a preferred embodiment of the present invention, a multi-modal cardiotherapy device. The device includes anti-arrhythmic means for delivering multiple modes of antiarrhythmic therapy to the heart. The device also includes cardiac contractility modulating means configured for delivering cardiac contractility modulating signals to the heart, for modulating the cardiac contractility of at least a portion of the heart, and for applying anti-arrhythmic cardiac contractility modulating signal therapy to the heart. The device also includes sensing means for sensing electrical signals related to cardiac activity sensed at the heart. The device also includes detecting means operatively connected to the sensing means for receiving the output signal of the sensing means and for detecting cardiac depolarization events of the heart. The device also includes controller means operatively connected to the antiarrhythmic means, the cardiac contractility modulating means and the detecting means, for processing the output of the detecting means to detect a cardiac arrhythmia or indications of possible arrhythmia, for controlling the application of the anti-arrhythmic therapy modes by the anti-arrhythmic means, and for controlling the application of the anti-arrhythmic cardiac contractility modulating signal therapy, and the modulating of the cardiac contractility by the cardiac contractility modulating means. The device also includes means for providing power to the anti-arrhythmic means, the cardiac contractility modulating means, the sensing means, the detecting means and the controller means.

Furthermore, in accordance with another preferred embodiment of the present invention, the anti-arrhythmic means is configured for delivering to the heart multiple modes of anti-arrhythmic therapy selected from anti-bradycardia pacing therapy, defibrillating shock therapy, cardioverting shock therapy, anti-tachycardia pacing therapy, variable energy shock therapy, and any combination thereof.

Furthermore, in accordance with another preferred embodiment of the present invention, the controller means is configured for coordinating the application to the heart of anti-arrhythmic therapy by the anti-arrhythmic means with the application to the heart of the anti-arrhythmic cardiac contractility modulating signal therapy by the cardiac contractility modulating means.

Furthermore, in accordance with another preferred embodiment of the present invention, the controller means is configured for coordinating the application to the heart of antiarrhythmic therapy by the anti-arrhythmic means with the modulating of the cardiac contractility by the cardiac contractility modulating means.

Furthermore, in accordance with another preferred embodiment of the present invention, the anti-arrhythmic means includes pacing means configured for pacing at least one chamber of the heart.

Furthermore, in accordance with another preferred embodiment of the present invention, the cardiac contractility modulating means is configured for controllably delivering cardiac contractility modulating signal anti-arrhythmic therapy to the heart by controllably delivering one or more of the cardiac contractility modulating signals to the heart for reducing the prevalence of arrhythmic episodes detected in the heart.

Furthermore, in accordance with another preferred embodiment of the present invention, the cardiac contractility modulating means is configured for modulating the cardiac output of the heart by delivering the cardiac contractility modulating signals to the heart.

Furthermore, in accordance with another preferred embodiment of the present invention, the controller means is configured for terminating the applying of cardiac contractility modulating signals to the heart prior to or upon the delivering to the heart of the anti-arrhythmic therapy.

Furthermore, in accordance with another preferred embodiment of the present invention, the controller means is configured for renewing the applying of cardiac contractility modulating signals to the heart after the delivering to the heart of the anti-arrhythmic therapy is terminated.

Furthermore, in accordance with another preferred embodiment of the present invention, the detecting means is configured for detecting T-wave alternans in the heart, as an indication of a possible cardiac arrhythmia.

Furthermore, in accordance with another preferred embodiment of the present invention, the device further includes electrode means operatively connected to the anti-arrhythmic means, the cardiac contractility modulating means and the sensing means, for delivering the anti-arrhythmic therapy to the heart, for applying the cardiac contractility modulating signals to the heart, and for sensing the electrical signals, respectively.

Furthermore, in accordance with another preferred embodiment of the present invention, the controller means is configured for determining the heart rate of the heart and for disabling the modulating of the cardiac contractility of the portion of the heart by the cardiac contractility modulating means within the duration of a cardiac contractility modulating signal free time period if the heart rate is larger than a first threshold value.

Finally, in accordance with another preferred embodiment of the present invention, the controller means is configured for enabling the modulating of the cardiac contractility of the portion of the heart by the cardiac contractility modulating means if no arrhythmia or indications of possible arrhythmia are detected within the duration of the cardiac contractility modulating signal free time period.

BRIEF DESCRIPTION OF THE DRAWINGS

The invention is herein described, by way of example only, with reference to the accompanying drawings, in which like components are designated by like reference numerals, wherein.

DETAILED DESCRIPTION OF THE INVENTION

The following terms are used throughout the application:

| Term | Definition |
| --- | --- |
| AC | Alternating Current |
| AGC | Automatic Gain Control |
| AICD | Automatic Internal Cardioverter Defibrillator |
| ATC | Automatic Threshold Control |
| ATP | Anti-Tachycardia Pacing |
| CCM | Cardiac Contractility Modulating |
| CHF | Congestive Heart Failure |
| CS | Coronary Sinus |
| DC | Direct Current |
| ECD | External Cardiac Defibrillator |
| ECG | Electro Cardiogram |
| ETC | Excitable Tissue Control |
| GCV | Great Cardiac Vein |
| ICD | Internal Cardiac Defibrillator |

-continued

| Term | Definition |
| --- | --- |
| IEGM | Intracardiac Electrogram |
| LUT | Look Up Table |
| LV | Left Ventricle |
| LVP | Left Ventricular Pressure |
| PVC | Premature Ventricular contraction |
| RA | Right Atrium |
| RV | Right Ventricle |
| SVT | Supra Ventricular Tachycardia |
| VF | Ventricular Fibrillation |
| EB's | Ectopic Beats |
| VT | Ventricular Tachycardia |

Figure 1:
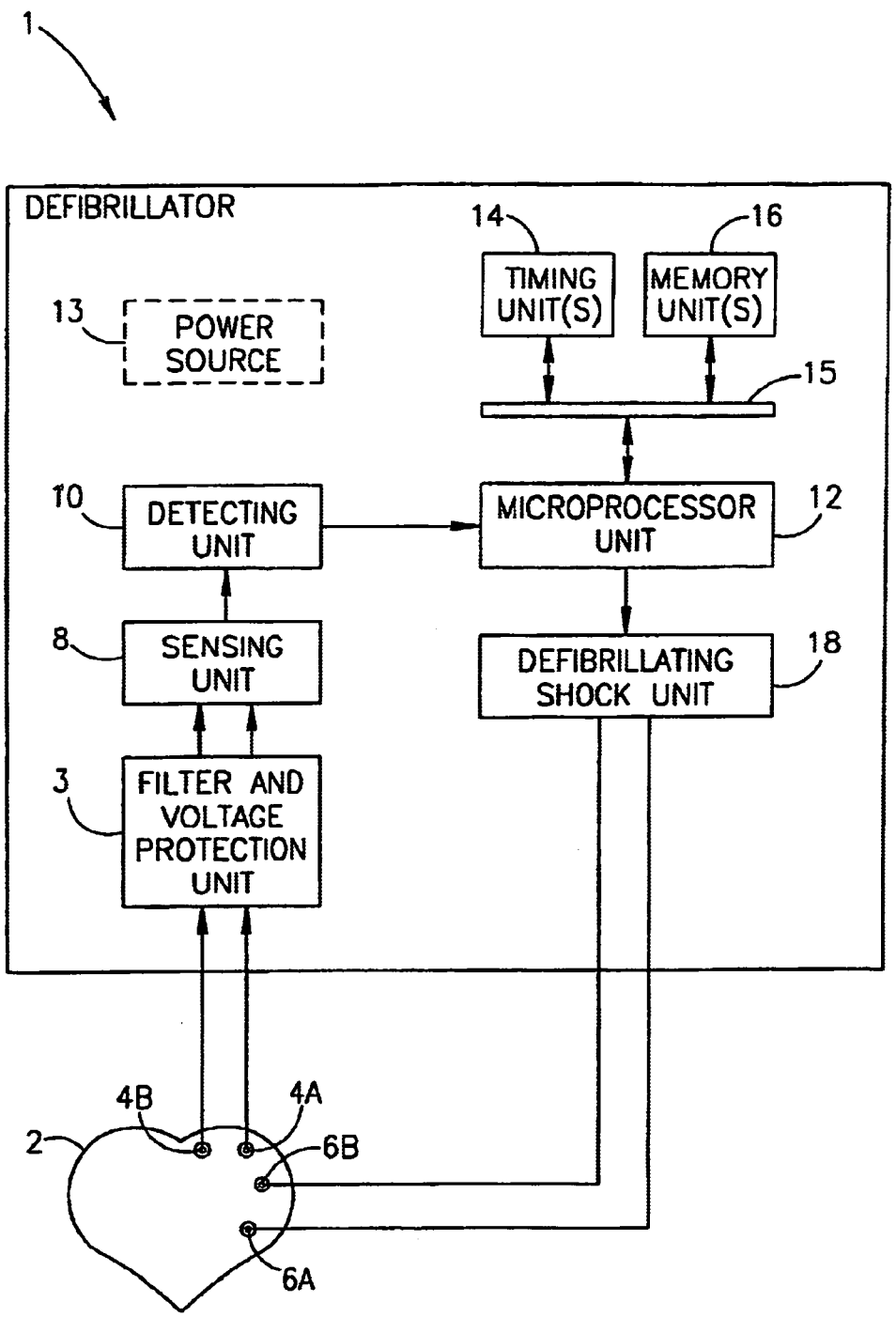
FIG. 1 is a schematic functional block diagram illustrating a prior art defibrillator device.

Reference is now made to FIG. 1 which is a schematic functional block diagram illustrating a prior art defibrillator device.

The defibrillator device 1 includes a filter and voltage protection unit 3 which is suitably electrically connected to sensing electrodes 4A and 4B which are implanted in or about the heart 2. The filter and high voltage protection unit 3 may includes various types of filtering circuitry for filtering the electrical signals sensed by the sensing electrodes 4A and 4B to remove signal components having undesirable frequencies (such as electrical noise at mains frequencies or other filterable noise) and for protecting the other circuitry of the defibrillator device 1 from high voltage signals resulting from the delivery of the electrical defibrillating shocks to the heart 2. The defibrillator 1 further includes a sensing unit 8 which is electrically connected to the filter and high voltage protecting unit 3.

The sensing unit 8 may include amplification circuitry for amplifying the filtered electrical signals. The output of the sensing unit 8 is suitably connected to a detecting circuit which performs the detection of electrical depolarization events representing cardiac activation. The detecting unit may be any analog or digital unit which is capable of detecting cardiac depolarization events by comparing it to a detection threshold as is known in the art or by any other event detection method which is known in the art. For example, the sensing unit 8 and the detecting unit 10 may be implemented using analog circuitry as disclosed by Dennis A. Brumwell et al. In Chapter 14 titled "THE AMPLIFIER: SENSING THE DEPOLARIZATION" of the book titled "IMPLANTABLE CARDIOVERTER DEFIBRILLATOR THERAPY: THE ENGINEERING-CLINICAL INTERFACE", pp. 275–302, Eds. Mark W. Kroll and Michael H. Lehmann, Kluwer Academic Publishers, USA, 1997, incorporated herein by reference. However, The sensing unit 8 and the detecting unit 10 may also be implemented by other different analog or digital circuits or any combinations thereof as is known in the art of defibrillators.

The defibrillator device 1 further includes a microprocessor unit 12 connected to the detecting unit 10 to receive therefrom signals representing the detection of cardiac depolarization events. The microprocessor unit 12 is also connected to Timing unit(s) 14 for receiving timing signals therefrom, and to memory unit(s) 16. The memory units 16 may be one or more memory devices for storing and retrieving data. The memory unit(s) 16 may include read-only memory devices and read-write memory devices for storage and retrieval of data. The timing unit(s) 14 and the memory unit(s) 16 communicate with the microprocessor unit 12 through a data bus 15.

The microprocessor 12 is also connected to a defibrillating unit 18 which is controlled by the microprocessor unit 12. The defibrillating shock unit 18 is designed to deliver electrical defibrillating shocks to the heart 2 through suitable defibrillating electrodes 6A and 6B disposed in or about the heart 2. The defibrillating shock unit 18 may typically include a current source such as a battery (not shown), a charging circuit (not shown), and high voltage output switches (not shown) as is known in the art. For example, the defibrillating shock unit 18 may be implemented as disclosed by C. G. Supino in Chapter 8, titled "THE SYSTEM" pp. 163–172 of the book titled "IMPLANTABLE CARDIO-VERTER DEFIBRILLATOR THERAPY: THE ENGINEERING-CLINICAL INTERFACE", Eds. Mark W. Kroll and Michael H. Lehmann, Kluwer Academic Publishers, USA, 1997, incorporated herein by reference. However, the defibrillator unit 18 may be implemented using any design or circuit for delivering defibrillation shocks to the heart which is known in the art.

The defibrillator device 1 also includes a power source 13 for providing power to the various components of the device 1. The power source 13 is suitably operatively connected (connections not shown for the sake of clarity of illustration) to provide electrical energy the components of the defibrillator device 1 as is known in the art. The power source 13 may be an electrochemical cell or a battery (primary or rechargeable), or the like but may be any other suitable power source for providing electrical power which is known in the art. It is noted that while the power source 13 is shown as included within the defibrillator device 1, the power source 13 may be also disposed externally to the device 1. For example, the power source 13 may be a power source such as, but not limited to, a conditioned or regulated DC or AC power supply, operatively connected to the mains power supply (not shown) as is known in the art. Such mains powered external defibrillator devices are well known in the art.

It is noted that the defibrillator device 1 of FIG. 1 is given herein by way of a non-limiting example of a prior art defibrillator and that many other types of defibrillators using different hardware implementations are possible as is known in the art.

The defibrillator device 1 represents an automatic implantable defibrillator device (AICD). However, other types of defibrillators such as external cardiac defibrillator (ECD) devices are also known in the art.

In operation, the sensing unit 8 amplifies the filtered electrical signals sensed by the sensing electrodes 4A and 4B, the detection unit 10 receives the amplified filtered signals and detects depolarization events, the detection may employ various methods such as threshold crossing detection methods as disclosed by Brumwell et al., including, but not limited to, AGC methods and ATC methods. However any other suitable event detection methods known in the art may also be used for event detection. The detecting unit 10 provides to the microprocessor unit 12 detection signals representative of the detection of an event in the sensed amplified signal provided by the sensing unit 8. The microprocessor unit 12 processes the detection signals using processing programs embedded in the microprocessor unit 12 or in the memory unit(s) 16 connected thereto. The various processing algorithms are generally referred to as classification algorithms or classification programs. The classification programs process the temporal data of the time of occurrence of the detection signals and classify the sensed cardiac rhythm as belonging to one of a plurality of possible cardiac rhythm categories. In a non-limiting example, the categories may include a range of heart rates defined as normal cardiac rate for a particular patient, an elevated heart rate range classified as a ventricular tachycardia (VT), and another elevated heart rate range classified as a ventricular fibrillation (VF). The various classification methods and algorithms are well known in the art are not the subject matter of the present invention and will therefore not be disclosed in detail hereinafter. Some exemplary methods of tachy-arrhythmia detection methods are disclosed by Stan M. Bach et al. in Chapter 15 titled "TACHYARRHYTHMIA DETECTION", pp. 303–323, of the book titled "IMPLANTABLE CARDIOVERTER DEFIBRILLATOR THERAPY: THE ENGINEERING-CLINICAL INTERFACE", Eds. Mark W. Kroll and Michael H. Lehmann, Kluwer Academic Publishers, USA, 1997, incorporated herein by reference.

If a VF episode is detected, the microprocessor 12 may based on such a detection output various control signals to the defibrillating shock unit 18 for initiating the charging of a high voltage capacitor (not shown) included in the defibrillating unit 18 in preparation for delivering a defibrillation shock to the heart. After verification of detection of VF further control signals output from the microprocessor unit 12 to the defibrillating unit 18 may initiate the delivering of a defibrillating, shock to the heart 2.

Some prior art defibrillator/cardioverter devices are also capable of delivering Anti-tachycardia pacing (ATP) and cardioversion therapy after detection of VT, as is well known in the art. For example, such devices and methods of delivering ATP and cardioversion therapy are disclosed in Chapter 16 titled "ANTI-TACHYCARDIA PACING AND CARDIOVERSION" pp. 325–342, of the book titled "IMPLANTABLE CARDIOVERTER DEFIBRILLATOR THERAPY: THE ENGINEERING-CLINICAL INTERFACE", Eds. Mark W. Kroll and Michael H. Lehmann, Kluwer Academic Publishers, USA, 1997, incorporated herein by reference. Such devices may utilize pacing circuitry (not shown in FIG. 1 for the sake of clarity of illustration) to deliver various pacing and shock signals to the heart for treating the ventricular tachycardia.

It is noted that the term Anti-arrhythmic devices is used throughout the present application to indicate devices for delivering anti-arrhythmia therapy to the heart, the anti-arrhythmia therapy may include defibrillating shocks suitable for VF termination, anti-arrhythmic pacing therapy suitable for treating tachy-arrhythmias such as supra-ventricular tachycardia (SVT) and other types of ventricular tachycardia (VT), cardioversion therapy, and any combination of the above therapies with pacing pulses for anti-bradycardia therapy.

Figure 2:
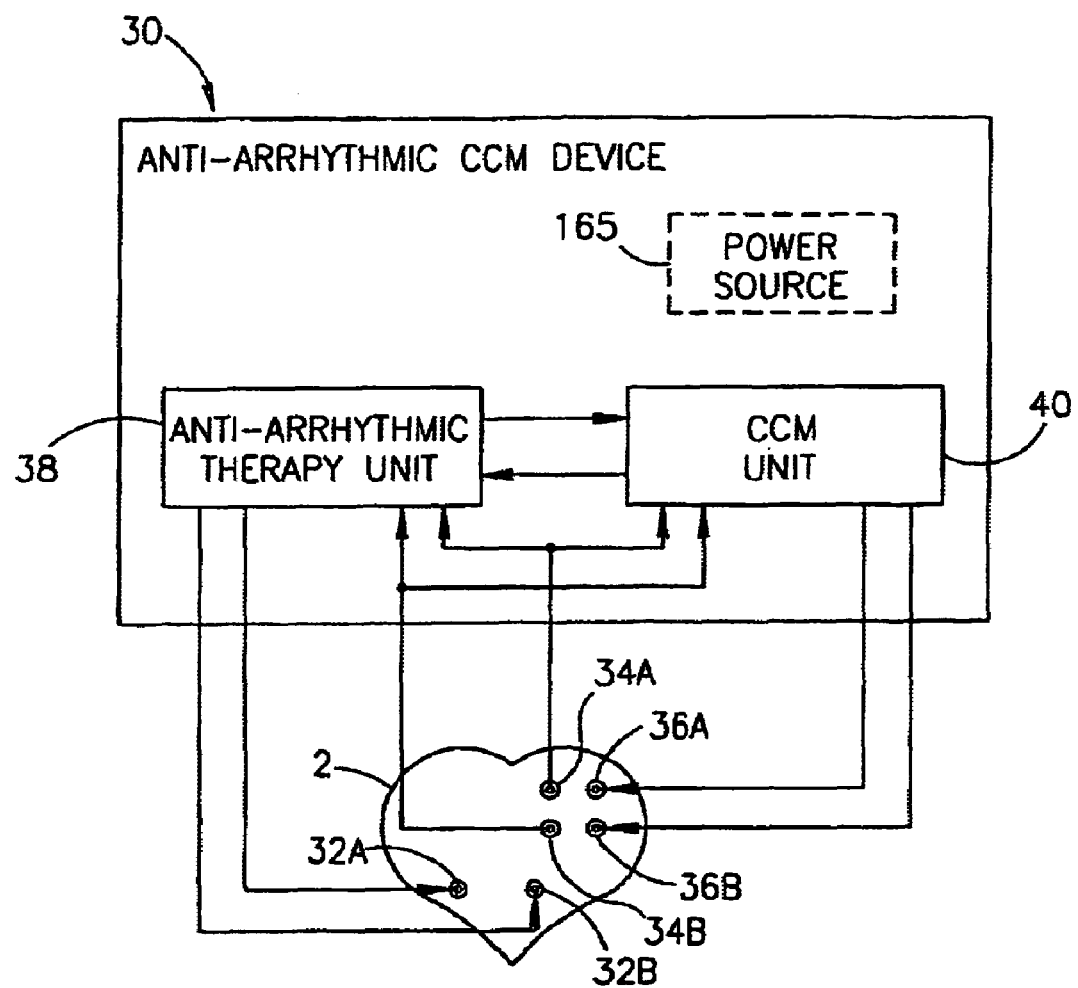
FIG. 2 is a schematic diagram illustrating a cardiac contractility modulating device having anti-arrhythmic therapy capabilities, in accordance with a preferred embodiment of the present invention.

Reference is now made to FIG. 2 which is a schematic diagram illustrating a cardiac contractility modulating device having anti-arrhythmic therapy capabilities, in accordance with a preferred embodiment of the present invention.

The anti-arrhythmic CCM device 30 includes an anti-arrhythmic therapy unit 38 and an a CCM unit 40. The anti-arrhythmic therapy unit 38 is operatively connected to the CCM unit 40 for receiving control signals therefrom. The anti-arrhythmic therapy unit 38 is connectable to sensing electrodes 34A and 34B for sensing cardiac depolarization events as disclosed hereinabove for prior art defibrillating devices. The anti-arrhythmic therapy unit 38 is also connectable to a pair of therapy delivering electrodes 32A and 32B, for delivering anti-tachycardia therapy to the heart 2 through the electrodes 32A and 32B as is known in the art and disclosed hereinabove. The anti-arrhythmic CCM device 30 also includes a power source 165 for providing power to the various components of the anti-arrhythmic CCM device 30. The power source 165 is suitably operatively connected (connections not shown for the sake of clarity of illustration) to provide electrical energy the components of the anti-arrhythmic CCM device 30, as is known in the art. The power source 165 may be an electrochemical cell or a battery (primary or rechargeable), or the like but may be any other suitable power source for providing electrical power which is known in the art. It is noted that while the power source 165 is shown as included within the anti-arrhythmic CCM device 30, the power source 165 may be also disposed externally to the anti-arrhythmic CCM device 30. For example, the power source 165 may be a power source such as, but not limited to, a conditioned or regulated DC or AC power supply, operatively connected to the mains power supply (not shown), as is known in the art.

For example, in accordance with one preferred embodiment of the present invention, the anti-arrhythmic therapy unit 38 is a defibrillating shock unit and the electrodes 32A and 32B are defibrillation electrodes suitable for delivering defibrillating shocks to the heart 2, as is known in the art and disclosed hereinabove.

Alternatively, in accordance with another preferred embodiment of the present invention, the anti-arrhythmic therapy unit 38 is an energy cardioverting shock unit and the electrodes 32A and 32B are cardiovertion electrodes suitable for delivering cardioverting shocks to the heart 2, as is known in the art and disclosed hereinabove.

In accordance with yet another preferred embodiment of the present invention, the anti-arrhythmic therapy unit 38 is a unit capable of delivering anti-tachycardia pacing (ATP) therapy and the electrodes 32A and 32B are pacing electrodes suitable for delivering ATP therapy pulses to the heart 2, as is known in the art and disclosed hereinabove.

Furthermore, accordance with yet another preferred embodiment of the present invention, the antiarrhythmic therapy unit 38 is a multi-modal anti-arrhythmic therapy unit capable of delivering cardioverting shock therapy, anti-tachycardia pacing (ATP) therapy, and defibrillating shock therapy. In such a case, more than one pair of therapy delivering electrodes (not shown) may need to be connected to the anti-arrhythmic therapy unit 38. For example, the electrodes 32A and 32B may be pacing electrodes suitable for delivering ATP therapy pulses to the heart 2, as is known in the art and disclosed hereinabove and additional electrodes (not shown) or electrodes pairs (not shown) may be suitably connected to the anti-arrhythmic therapy unit 38, such as defibrillating electrodes (not shown) and/or defibrillating/cardioverting electrodes (not shown).

The CCM unit 40 is connectable to a pair of CCM electrodes 36A and 36B (also known as ETC electrodes) and is capable of delivering CCM signals (also known in the art as ETC signals) to the heart through the CCM electrodes 36A and 36B to modulate cardiac contractility as disclosed by Ben Haim et al. and by Mika et al. In the PCT publications and applications, and in the Co-pending US patent applications referenced hereinabove. It is noted that, the anti-arrhythmic therapy unit 38 may be any anti-arrhythmia therapy device known in the art and may be implemented as an analog unit; a digital unit or a hybrid analog and digital unit.

It will be appreciated by those skilled in the art that the anti-arrhythmic CCM device 30 of FIG. 2 may also be adapted to include a pacing unit (not shown). Such a pacing unit may be used in conjunction with suitable pacing electrodes (not shown) for pacing the heart 2, for example, in patients in need of anti-bradycardia pacing. Additionally, the pacing unit (not shown) may be integrated in the anti-arrhythmic therapy unit 38 such that it may be used for delivering ATP therapy if the need for such therapy is detected by the anti-arrhythmic therapy unit 38, as is known in the art and disclosed in U.S. Pat. No. 4,830,006 to Haluska et al.

It is noted that while the anti-arrhythmic therapy unit 38, is illustrated as being connected to a single pair of sensing electrodes 34A and 34B, a single pair of electrodes 32A and 32B for delivering anti-tachycardia therapy to the heart 2, and a single pair of CCM electrodes for delivery of CCM signals to the heart 2, many other electrode configurations and combinations are possible which are all considered to be within the scope of the present invention. For example, the antiarrhythmic therapy unit 38 may be connected to more than one CCM delivering electrode pair or electrodes (not shown) for delivering CCM signals to more than one cardiac region. In another example, more than one pair of sensing electrodes or a plurality of single sensing electrodes (not shown) may be used for enabling multi chamber sensing and/or pacing, such multi-electrode configurations are disclosed in the above referenced, PCT publications to Ben Haim et al. and in co-pending U.S. patent applications Ser. Nos. 09/276,460, 09/328,068 and 09/338,649 to Mika et al., and in the corresponding PCT applications.

It is noted that many types of sensing electrodes, pacing electrodes, shock therapy delivering electrodes may be used in conjunction with the anti-arrhythmic CCM device 38 of FIG. 2. Such electrodes are known in the art and may also be commercially obtained. The electrode types have to be suitably adapted to the design and implementation of the device anti-arrhythmic CCM device 38. For example if the device 38 is adapted for use in an intensive care unit it may use epicardial electrodes or other external types of electrodes. In chronically implanted devices, the electrodes may be intracardiac electrodes adapted for sensing, pacing, defibrillation shock delivery electrodes or any other types of anti-arrhythmia therapy electrodes known in the art.

Preferably, the anti-arrhythmic therapy unit 38 and the CCM unit are both in communication with a common microprocessor unit (not shown in FIG. 2, For the sake of clarity of illustration). In such a case, the microprocessor unit (not shown) controls the delivery of CCM signals by the CCM unit 40 and also sends control signals to the anti-arrhythmic therapy unit 38. The control signals sent from the microprocessor unit (not shown) control the anti-arrhythmic therapy unit 38 to prevent the interference of the CCM signal induced electrical artifacts from interfering with the detection of cardiac arrhythmias as is disclosed in detail hereinafter. Alternatively, the anti-arrhythmic therapy unit 38 and the CCM unit 40 may each include a dedicated microprocessor unit (the microprocessor units are not shown in FIG. 2, for the sake of clarity of illustration). In the latter case the microprocessor unit (not shown) of the antiarrhythmic therapy unit 38 is in communication with the microprocessor unit (not shown) of the CCM unit 40 to provide the microprocessor unit of the anti-arrhythmic therapy unit 38 with data representative of the time of delivery of CCM signals by the CCM unit 40. This data is processed by the microprocessor of the anti-arrhythmic therapy unit 38, or by the microprocessor of the CCM unit 40 or by both of these microprocessors to prevent the interference of the CCM signal induced electrical artifacts from interfering with the detection of cardiac arrhythmias as is disclosed in detail hereinafter.

Briefly, in accordance with a preferred embodiment of the present invention the control signals may be used to prevent the sensing of CCM signal induced artifacts at the sensing level.

In accordance with another preferred embodiment of the present invention the control signals may be used to prevent the sensing of CCM signal induced artifacts at the detecting level.

In accordance with yet another preferred embodiment of the present invention the control signals may be used to prevent the sensing of CCM signal induced artifacts at the sensing and the detecting level simultaneously.

Alternatively, in accordance with yet another preferred embodiment of the present invention the control signals may be used to prevent the interference of the CCM signal induced electrical artifacts from interfering with the detection of cardiac arrhythmias, not by preventing the sensing or the detecting of the CCM signal induced electrical artifact but by correcting or compensating the error introduced by detection of the CCM induced artifacts as cardiac events at the arrhythmia classification program level. This correction or compensation is achieved computationally by suitably processing the control signals indicative of the delivery of an ETC signal.

In operation, the CCM unit 40 may operate to deliver CCM signals to the heart through the CCM electrodes 36A and 36B or through any other pair (not shown) or pairs (not shown) of electrodes applied to more than one cardiac site. The Pair of sensing electrodes 34A and 34B may be commonly used for feeding the sensed signals to the sensing unit (not shown) of the anti-arrhythmic therapy unit 38 and to the sensing unit (not shown) of the CCM unit 40. Alternatively, different separate pairs of electrodes (not shown) may be used for sensing by each of the anti-arrhythmic therapy unit 38 and the CCM unit 40. Prior to the delivery of CCM signals to the heart 2, the CCM unit 40 or the microprocessor (not shown in FIG. 2) which controls the CCM unit 40 delivers control signals to the anti-arrhythmic therapy unit 38. These control signal are related to the delivery of the CCM signals and are used by the anti-arrhythmic therapy unit 38 to disable the sensing of the CCM related electrical artifacts or to disable the detection of these artifacts as cardiac depolarization events.

It is noted that, additional control signals may also be delivered to the anti-arrhythmic therapy unit 38 during the delivery of a CCM signal to the heart if the method of filtering the artifact signal is employed at the level of a signal filtering unit (not shown) as is disclosed in more detail hereinafter.

Figure 3:
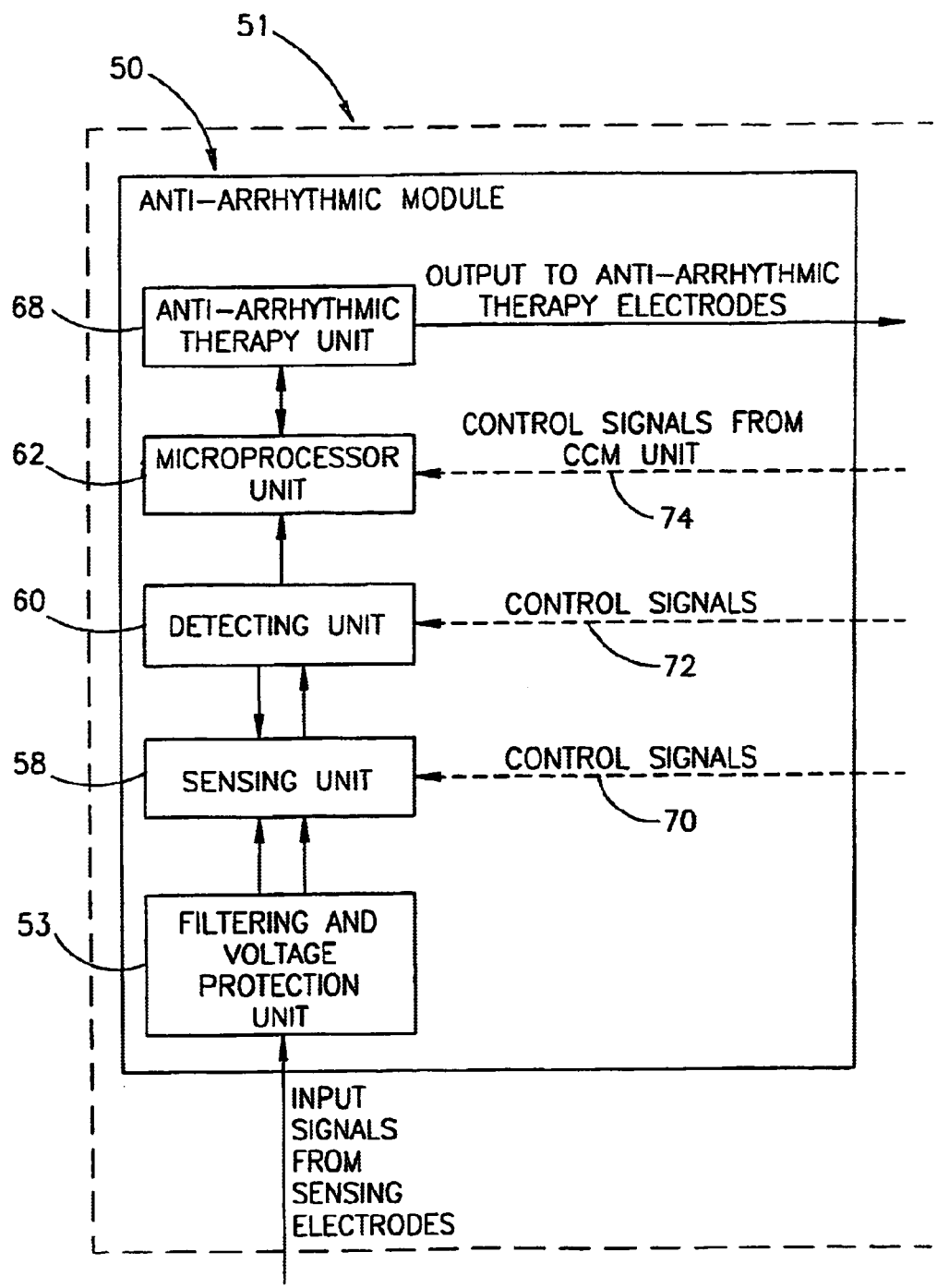
FIG. 3 is a schematic diagram illustrating a detail of a cardiac contractility modulating device having anti-arrhythmic therapy capabilities, useful in understanding possible implementation methods of control signals at different levels of a part of the cardiac contractility modulating device of the present invention.

Reference is now made to FIG. 3 which is a schematic diagram illustrating a detail of a cardiac contractility modulating device having anti-arrhythmic therapy capabilities, useful in understanding possible implementation methods of control signals at different levels of a part of the cardiac contractility modulating device of the present invention.

In FIG. 3, an anti-arrhythmic module 50 is illustrated which is integrated within a CCM anti-arrhythmic device 51 (only a part of the device 51 is shown, for the sake of clarity of illustration). The module 50 includes a filtering and voltage protection unit 53, which receives input signals from sensing electrodes (not shown) disposed in or about the heart and is connected to a sensing unit 58. The filtering and voltage protection unit 53 is operative to filter the signals from the sensing electrodes and to protect the sensing unit 58 connected thereto from the high energy defibrillating shock related signals, as is known in the art and disclosed hereinabove.

The sensing unit 58 amplifies the signal received from the sensing electrodes (not shown) The sensing unit 58 is connected to a detecting unit 60 which detects depolarization events in the filtered amplified signals at the output of the sensing unit 58 as disclosed in detail hereinabove for the prior art defibrillator 1 of FIG. 1. The detecting unit 60 is operatively connected to a microprocessor unit 62.

The microprocessor unit 62 is operatively connected to an anti-arrhythmic therapy unit 68 and controls the delivery of anti-arrhythmic therapy signals to the heart 2 by controlling the output of anti-arrhythmic therapy signals from anti-arrhythmic therapy unit 68. The anti-arrhythmic therapy unit 68 may be any type of device or unit known in the art for delivering one or more anti-arrhythmic type of therapy to the heart. For example, the anti-arrhythmic therapy unit 68 may be a defibrillator unit, a cardioverter/defibrillator unit, or a multi-modal cardiac therapy unit similar to the cardiac stimulator disclosed by Haluska et al. in U.S. Pat. No. 4,830,006, or any other type of anti-arrhythmic therapy unit known in the art.

The anti-arrhythmic module 50 receives control signals from other parts (not shown in detail) of the CCM device 51 within which it is integrated. The control signals may be received from the CCM unit (not shown) which is also integrated within the CCM device 51, or from a microprocessor or controller unit (not shown) which is included in or communicating with the CCM unit (not shown). Alternatively, the microprocessor unit 62 may control the entire CCM device 51, including the CCM unit (not shown).

The prevention of interference of the sensed CCM signal induced electrical artifacts may be implemented in various ways. In accordance with one preferred embodiment of the present invention, the prevention of interference is implemented at the sensing level. In this implementation, suitable control signals are sent to the sensing unit 58 prior to the delivery of each CCM signal to the heart 2. These control signals are represented by the dashed arrow 70. Each of the received control signals causes the sensing unit 58 to become refractory to incoming input signals from the filtering and voltage protecting unit 53. The timing and duration of the control signals are such that the sensing unit 58 becomes refractory to incoming input signals before the delivery of the CCM signal to the heart and stays refractory for a refractory period having a duration that is sufficient to prevent the CCM induced electrical artifact from being detected as an event by the detection unit 60. Thus, the refractory period of the sensing unit 58 may last longer than the duration of the CCM signal delivered to the heart, to accommodate for the precise shape, amplitude, polarity and duration of the CCM induced artifact as it is sensed by the sensing unit 58. The duration of the refractory period may be a fixed duration, or may be a preset duration that may be programmed, telemetrically or non-telemetrically, into the memory (not shown) of the CCM device 51 based on actual determination of the artifact parameters obtained from each individual patient in a recording and measurement session taking place after implantation of the electrodes in the patient.

Thus, the determination of the duration of the refractory period is done such as to take into account the maximal duration of CCM signal induced electrical artifact which may be picked up by the sensing electrodes (not shown) and is capable of being erroneously detected as a true event in the patient in which the device 51 is operative. This maximal duration is preferably determined empirically for each patient by a physician or cardiologist after collecting data in a test session of the device 51 in the patient taking place after electrode implantation. It is also preferred to add a certain safety margin by increasing the refractory period above the value of the empirically determined maximal duration, this safety margin may be advantageous in preventing erroneous event detection in cases in which the CCM signal induced electrical artifact has large variability or may show drift over extended periods of time due to electrode movements or other reasons.

It is noted that some CCM devices may apply to the heart of the same patient different types of CCM signals having different or varying signal parameters, in response to different cardiac conditions or for changing and controlling the contractility and cardiac output of the heart. The CCM signal parameters that may vary include, but are not limited to, CCM signal amplitude, CCM signal duration, CCM signal waveform, and CCM signal polarity.

Thus, if the refractory period duration is a fixed duration, care must be taken to select such a duration that is long enough to ensure that any type of CCM signal which the device 51 is capable of delivering to the heart will not result in erroneous (spurious) detection of the CCM signal induced electrical artifact as a detected event. Alternatively, the refractory period may be a variable refractory period and the device 51 may be adapted to select a particular value of a refractory period duration from a preprogrammed look up table (LUT), which includes different refractory period duration values associated with different CCM signal types. The data in the LUT may be obtained by empirical tests performed in the patient in a testing or data collection session after implantation of the electrodes in each individual patient. Such tests may record the parameters of the electrical artifacts associated with the delivery of cardiac contractility modulating signals having different parameters. The parameters of the recorded electrical artifacts may then be used to determine appropriate refractory period parameter sets for each different type of deliverable CCM signal to prevent erroneous detection of the electrical artifacts as cardiac events, as disclosed in detail hereinabove. This method has the advantage of being individually adapted to each patent, and of enabling the control of the refractory period on a beat by beat basis.

The sensing unit 58 may receive the control signals from the microprocessor unit which controls the activation of the CCM unit. In the embodiment in which the device 51 includes only one microprocessor unit 62, the sensing unit 58 receives the control signals from the microprocessor unit 62. If the CCM unit (not shown) of the device 51 is controlled by a second microprocessor or controller (not shown) which is not the microprocessor 62, the control signals for controlling the refractory period of the sensing unit 58 may be received from the second microprocessor or controller.

In accordance with another preferred embodiment of the present invention, the prevention of interference is implemented at the detecting level. In this implementation, suitable control signals are sent to the detecting unit 60 prior to the delivery of each CCM signal to the heart 2. These control signals are represented by the dashed arrow 72. Each received control signal causes the detecting unit 60 to become refractory to incoming input signals from the sensing unit 58. The timing and duration of the control signals are such that the detecting unit 60 becomes refractory to incoming input signals before the delivery of the CCM signal to the heart and stays refractory for a refractory period having a duration that is sufficient to prevent the CCM induced electrical artifact from being detected as an event by the detection unit 60. Thus, the refractory period of the detecting unit 60 may last longer than the duration of the CCM signal delivered to the heart, to accommodate for the precise shape, amplitude and duration of the CCM induced artifact as it is sensed by the sensing unit 58. The duration of the refractory period of detecting unit 60 may be a fixed duration, or may be a preset duration that may be programmed, telemetrically or non-telemetrically, into the memory (not shown) of the device 51 based on actual determination of the maximal artifact parameters obtained from each individual patient in a recording and measurement session taking place after implantation of the electrodes in the patient.

Similar to the refractory period of the sensing unit 58 disclosed hereinabove, if the refractory period duration of the detecting unit 60 is a fixed duration, care must be taken to select such a duration that is long enough to ensure that any type of CCM signal which the device 51 is capable of delivering to the heart will not result in erroneous (spurious) detection of the CCM signal induced electrical artifact as a detected event. Alternatively, the refractory period of the detecting unit 60 may be a variable refractory period and the device 51 may be adapted to select a particular value of a refractory period duration from a preprogrammed look up table (LUT) which includes different refractory period duration values associated with different CCM signal types. The data in the LUT may be obtained by empirical tests performed in the patient in a testing or data collection session after implantation of the electrodes in each individual patient. Such tests may record the parameters of the electrical artifacts associated with the delivery of cardiac contractility modulating signals having different parameters. The parameters of the recorded electrical artifacts may then be used to determine appropriate refractory period parameter sets for each different type of deliverable CCM signal to prevent erroneous detection of the electrical artifacts as cardiac events, as disclosed in detail hereinabove. This method has the advantage of being individually adapted to each patient, and of enabling the control of the refractory period on a beat by beat basis. The method is adapted for use in CCM devices which are capable of delivering variable CCM signals and of adapting one or more of the CCM signal parameters (such as but not limited to the amplitude, duration, wave shape, and polarity of the CCM signal) for controlling the effect of the CCM signals on the cardiac contractility and/or on the cardiac output. In accordance with a preferred embodiment of the present invention, since in such CCM devices, the CCM signals parameters may be varied in time according to, inter alia, detected patent need and patient metabolic state, the microprocessor unit 62 may select from the LUT the appropriate refractory period parameters which are associated with the parameters of the particular CCM signal which is about to be delivered to the heart of the patient under the control of the microprocessor unit 62. This method has the advantage of being individually adapted to each patient and of flexibly and automatically allowing the selection of refractory period duration which is adapted to the parameters of the currently delivered CCM signal parameters, thus, allowing control of CCM signal parameters while still efficiently preventing erroneous detection of the CCM induced electrical artifacts as true events.

The detecting unit 60 may receive the control signals from the microprocessor unit which controls the activation of the CCM unit. In the embodiment in which the device 51 includes only one microprocessor unit 62, the detecting unit 60 receives the control signals from the microprocessor unit 62. If the CCM unit (not shown) of the device 51 is controlled by a second microprocessor or controller (not shown) which is not the microprocessor 62, the control signals for controlling the refractory period of the detection unit 60 may be received from the second microprocessor or controller.

It is noted that, the microprocessor unit 62 may be a microprocessor unit which is dedicated to the module 50 or may be a microprocessor unit which is commonly used to control the operation of the entire CCM device 51.

Furthermore, in accordance with another preferred embodiment of the present invention, the control signals may cause the sensing unit 58 and the detecting unit 60 to become refractory as disclosed hereinabove. This implementation has the advantage that more power is conserved by putting both the sensing unit 58 and the detecting unit 60 into a refractory state since the power consumption of each of these units is smaller in the refractory period, resulting in increasing the useful life of the battery (not Shown) or power source (not shown) which powers the device 51.

It is further noted that the preventing of the sensing and/or the detecting of CCM induced electrical artifacts as event may also be achieved by controlling the filtering and voltage protection unit 53 such as by putting it into a refractory period or by suitably controlling the filtering properties thereof such that all the signals fed into the sensing unit 58 including the CCM related electrical artifact signals are strongly attenuated during a period equivalent to the duration of the above disclosed refractory period. If the method of preventing the sensing and/or the detecting of CCM induced electrical artifacts as true events is achieved by controlling the filtering characteristics such as but not limited to the frequency response characteristics of the filtering and voltage protection unit 53, the microprocessor unit 62 which controls the filtering and voltage protection unit 53 and/or the CCM unit (not shown) of the device 51 may also provide the filtering and voltage protection unit 53 with data related to the CCM signal parameters, such as but not limited to CCM signal amplitude, CCM signal duration, CCM signal waveform, and CCM signal polarity. This CCM signal parameter related data may be provided by the microprocessor unit 62 to the filtering and voltage protection unit 53 before and/or during the time of delivery of the CCM signals to the heart. The CCM signal parameter related data is useful particularly in cases where one or more of the parameters of the CCM signals is dynamically varied under control of the microprocessor 62, during the delivery of CCM therapy, because such CCM signal parameter related data allows the control of the filtering characteristics of the filtering and voltage protection unit 53 on a beat by beat basis for CCM signals having dynamically variable parameters.

It is noted that the filtering and voltage protection unit 53 may be adapted to function as a controlled matched filter which is adapted to reject the CCM signal induced electrical artifact based on a fixed or dynamically varying template or data adapted for maximal rejection of the predicted waveform and/or frequency content of the CCM induced electrical artifact. Such template or data may be supplied to the filtering and voltage protection unit 53 by the microprocessor 62 in accordance with the data of the type and parameters of the CCM signal scheduled to be delivered to the heart in accordance with the CCM delivery control program operative on the microprocessor unit 62.

In accordance with still another preferred embodiment of the present invention, the prevention of interference of the CCM induced electrical artifact signals is implemented at the classification level. In this implementation, the sensing unit 58 and the detecting unit 60 are not put into a CCM signal related refractory period. The microprocessor 62 may receive control signals represented by the dashed arrow 74 from the CCM unit. These control signals are indicative of the timing of delivery of the CCM signals to the heart. Alternatively, in cases wherein the microprocessor 62 also controls the activation of the CCM unit (not shown) of the device 51, the microprocessor 62 has internal data therewithin indicative of the computed timing of activation of the CCM unit. In both of these alternatives the microprocessor unit 62 uses the data indicative of the timing of the delivery of CCM signals for computationally correcting or compensating for the possible errors in computing the heart rate which may be induced by spurious detection of the CCM signal induced artifact as "true" depolarization events. In a non-limiting example, the classification program may subtract the known number of CCM signals delivered to the heart within a certain number of cardiac beat cycles from the total number of events detected by the detesting unit 60 within the same beat cycles, preventing possible heart rate classification errors which may have been introduced by an erroneous number of detected events, had the correction not been applied.

It will be appreciated that the correction methods which may be used for correcting or compensating for erroneous event detection prior to processing the data for classification and arrhythmia detection must be adapted to the specific methods, programs and algorithms which are used for processing the event detection data and for the classification of heart rates for arrhythmia detection and classification.

It is noted that, while the method of triggering or inducing a refractory period in one or more of the sensing unit 58, the filtering and voltage protection unit 53 and the detecting unit 60 may provide an adequate solution to the problem of erroneous CCM induced artifact detection, care must be taken to ensure that the blanking of one or more of the sensing unit 58, the filtering and voltage protection unit 53 and the detecting unit 60 during the imposed refractory period will not by itself produce undesirable errors in the estimation of the heart rate due to the cessation of detection of any electrical events within the imposed refractory period duration. Typically, the CCM signal duration may vary between approximately 20–50 milliseconds (although lower or higher duration values may also be used). Some VT episodes in human cardiac patients may exhibit R—R intervals of approximately 250–300 millisecond duration. Therefore, when the above disclosed refractory period method is used, the blanking or refractory period may occupy approximately 20% of the total beat cycle. Thus, it is a definite possibility that a true event may occur within the refractory period and will therefore not be detected, which may cause errors in the determination of the heart rate. Such errors may eventual lead to wrong classification of the heart rate by the classification methods or classification algorithms used and may also undesirably delay or in extreme cases even prevent the delivery of the proper anti-arrhythmic therapy by the anti-arrhythmic module 50 of the device 51. For example, under such circumstances, an episode of VT may be missed of misclassified as allowable tachycardia, and VF may be misclassified as VT leading to delay in delivery of the proper type of anti-arrhythmic therapy or to failure to deliver any tachy-arrhythmic therapy.

In order to prevent or at least to reduce the probability of the misclassification and the resulting delay or failure of the proper application of anti-arrhythmic therapy, the device 51 may be adapted to use a threshold based method to disable the delivery of CCM signals to the heart when the detected heart rate exceeds a certain threshold. Thus, in accordance with another preferred embodiment of the present invention, the device 51 continuously determines the heart rate and classifies the heart rate, in accordance with any sensing, detecting, and anti-arrhythmic heart rate classification methods or algorithms known in the art. Simultaneously, the CCM unit or circuitry operates to detect the need for CCM therapy and to control the delivery of CCM signals to the heart, in accordance with any of the methods of CCM signal delivery known in the art or disclosed in any of the above referenced published or co-pending patent applications disclosed hereinabove. If the heart rate exceeds a certain threshold level, this is classified as a suspected tachyarrhythmia and the microprocessor 62 disables the delivery of CCM signals to the heart within a time period which is referred to as the "CCM signal free" period, hereinafter. The device 51 then continues to determine the heart rate within this CCM signal free period, in the absence of CCM signal delivery. The device 51 analyzes and classifies the heart rate in accordance with the classification criteria based on the detection data obtained by the device 51 during the CCM signal free period. The device 51 then determines whether any type of anti-arrhythmia therapy is to be delivered to the heart based on the classification of the heart rate obtained in the CCM free period.

If the classification of the heart rate obtained in the CCM free period indicates the need to deliver any type of anti-arrhythmic therapy, the device 51 continues the disabling of CCM signal delivery and initiates the delivery of the required anti-arrhythmic therapy, and continues to deliver any indicated anti-arrhythmic therapy and to determine the heart rate as is known in the art until the anti-arrhythmic therapy is terminated. If the anti-arrhythmic therapy is terminated by the device 51, the device 51 enables the delivery of CCM signals to the heart.

If the classification of the heart rate obtained in the CCM free period does not indicate a need to deliver any type of anti-arrhythmic therapy, the device 51 enables the delivery of CCM signals.

Thus, in the above disclosed method of operation of the device 51, the ant-arrhythmic detection and classification program, sub-routine or algorithm takes priority over the CCM delivery control program, sub-routine or algorithm, enabling it to override, interrupt or disable the CCM signal delivery even under conditions in which the delivery of CCM signals is called for by the CCM delivery control program to modify cardiac contractility and or cardiac output.

Figure 4:
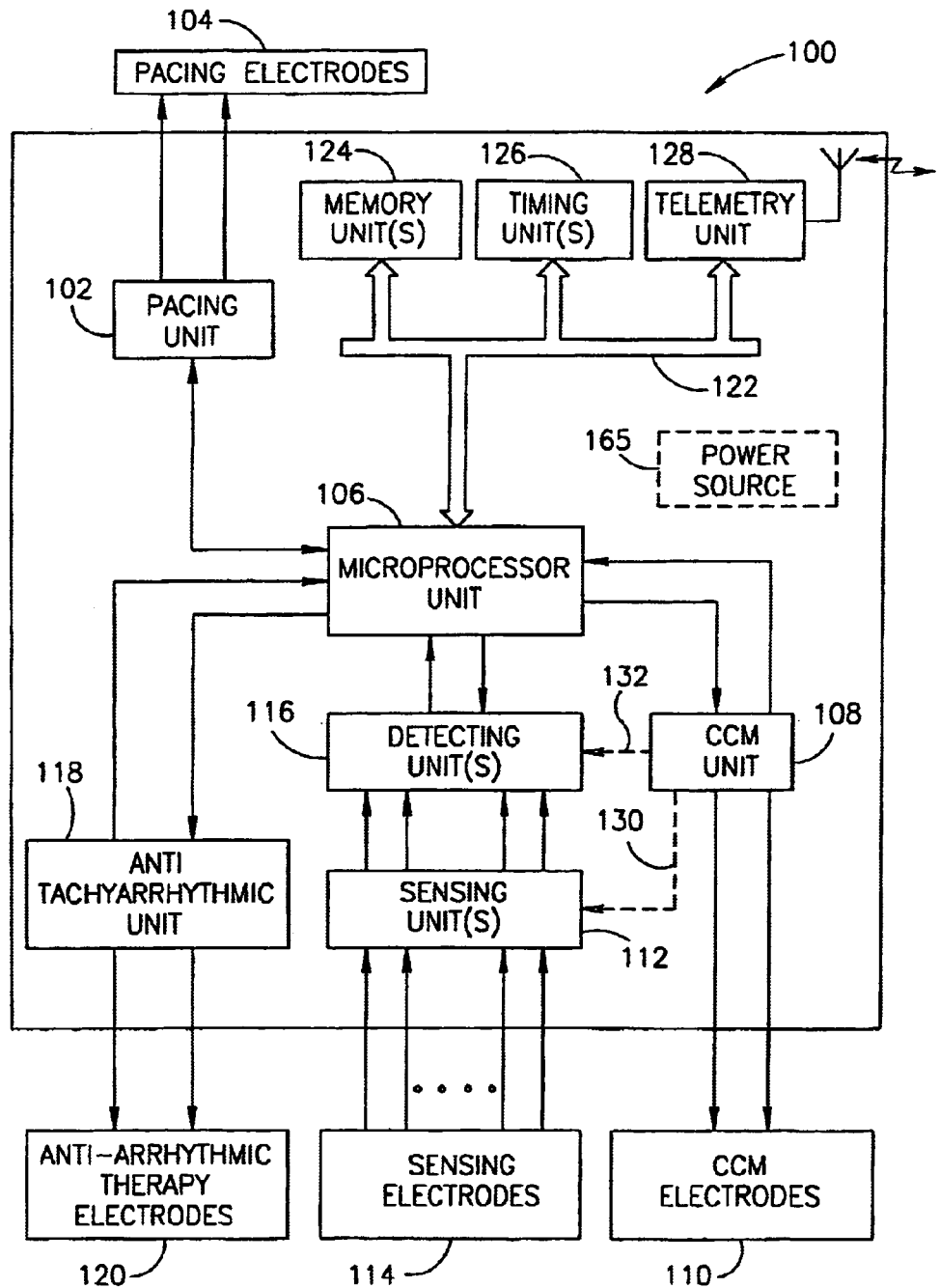
FIG. 4 is a schematic diagram illustrating a CCM device having capability of applying a plurality of different anti-arrhythmic therapy methods to the heart, in accordance with another preferred embodiment of the present invention.

Reference is now made to FIG. 4 which is a schematic diagram illustrating a CCM device having capability of applying a plurality of different anti-arrhythmic therapy methods to the heart.

The CCM device 100 of FIG. 4 includes a pacing unit 102 connectable to one or more pacing electrodes 104. The pacing unit is suitably connected to a microprocessor or controller 106. The microprocessor 106 controls the pacing unit to deliver pacing pulses to the heart (nor shown) for performing anti-bradycardia pacing if necessary, as is well known in the art. The CCM device 100 also includes a CCM unit 108 capable of delivering CCM signals (also known in the art as ETC signals). The CCM unit 108 is connectable to one or more CCM electrodes 110 for delivering CCM signals to the heart. The CCM device 100 also includes sensing units 112 connectable to one or more sensing electrodes 114 for sensing electrical signals at or about the heart. The CCM device 100 also includes one or more detecting units 116 which are connected to the sensing unit(s) 112 for receiving amplified sensed signals therefrom and to the microprocessor 106 for providing control signals thereto indicative of detecting depolarization events in the heart. The CCM device 100 also includes an anti-tachyarrhythmic unit 118 which is connected to the microprocessor 106 for receiving control signals therefrom. The anti-tachyarrhythmic unit 118 is connectable to one or more anti-arrhythmic therapy electrodes 120 for delivering anti-arrhythmic therapy to the heart.

The microprocessor unit 106 controls the output of anti-arrhythmic therapy signals from the anti-tachyarrhythmic unit 118. The anti-tachyarrhythmic unit 118 may be any type of device or unit known in the art for delivering one or more anti-arrhythmic type of therapy to the heart. For example, the anti-arrhythmic therapy unit 68 may be a defibrillator unit, a cardioverter/defibrillator unit or a multi-modal cardiac therapy unit similar to the cardiac stimulator disclosed by Haluska et al. in U.S. Pat. No. 4,830,006, or any other type of anti-arrhythmic therapy unit known in the art.

The anti-arrhythmic electrodes 120 are adapted to be suitable for the delivery of the specific types of antiarrhythmic therapy signals which the anti-tachyarrhythmic unit 118 is capable of applying to the heart. For example, the anti-arrhythmic electrodes 120 may comprise one or more electrodes adapted for delivering signals to the heart such as, but not limited to, high energy defibrillating shock signals, non-defibrillating cardioversion signals, ATP signals, and the like. The microprocessor unit 106 is suitably connected to a data bus 122. The data bus 122 is connected to one or more memory units 124, one or more timing units 126 and to a telemetry unit 128. The microprocessor unit 106 may store and retrieve data on the memory units 124. The memory units 124 may include memory units including embedded read only data such as programs for operating the microprocessor unit 106 to control and operate the device 100. The memory units 124 may also include memory units having read and write capabilities for data storage and retrieval (such as, but not limited to, RAM memory units) for storing, inter alia, patient data, computational results, and programming instructions which are telemetrically or non-telemetrically communicated to the CCM device 100. The timing units 128 provide timing or clocking signals to the microprocessor unit 106 over the data bus 122. The microprocessor unit 106 communicates with the memory units 124, the timing unit(s) 126 and the telemetry device 128 over the data bus 122. The telemetry device 128 is optional and enables wireless data transmission to and from a telemetry transceiver unit (not shown) disposed outside the patient (not shown).

In operation, the delivery of CCM signals to the heart by the CCM unit 108 is controlled based on the output of the detecting units 112 to the microprocessor unit 106, as disclosed in detail in the above referenced co-pending U.S. patent application Ser. Nos. 09/276,460, 09/328,068 and 09/338,649 to Mika et al., and in the corresponding PCT applications.

In accordance with one preferred embodiment of the present invention, the CCM unit 108 provides control signals to one or more of the sensing units 112 and/or to one or more of the detecting units 116 for inducing refractory periods in the sensing unit(s) 112 or in the detecting units 116 or in the sensing unit(s) 112 and the detecting units 116 as disclosed in detail hereinabove, for preventing interference of CCM induced electrical artifact signals with the sensing or the detecting or both sensing and detecting of depolarization events as disclosed hereinabove. The control signals may be (optionally) provided from the CCM unit 108 to the sensing unit 112 as represented by the dashed arrow 130. The control signals may also be (optionally) provided from the CCM unit 108 to the detecting unit(s) 116 as represented by the dashed arrow 132. The control signals may also be simultaneously provided to the sensing unit(s) 112 and to the detecting unit(s) 116 as disclosed hereinabove.

Alternatively, in accordance with another preferred embodiment of the present invention, the control signals may be provided from the microprocessor unit 106 to the sensing unit(s) 112 or to the detecting unit(s) 116 or to both of the sensing unit(s) 112 and the detecting unit(s) 116 as disclosed in detail hereinabove. The sensing unit(s) 112 or the detecting unit(s) 116 or both the sensing unit(s) 112 and the detecting unit(s) 116 may be switched by the control signals into a refractory state as disclosed hereinabove.

Furthermore, in accordance with yet another preferred embodiment of the present invention, the microprocessor unit 106 may use the data of the timing of the delivery of CCM signals to the heart for performing a correcting or compensating method or computation in order to prevent errors at the classification level as disclosed in detail hereinabove.

It is noted that, the sensing units 112 may include a plurality of sensing units operative for providing sensing at different sites of the heart, such as but not limited to, the right atrium, the right ventricle, the left ventricle of the heart and other different cardiac sites in order to provide the various sensing configurations required for the operation of any of the specific type or configuration of the anti-tachyarrhythmic unit 118 which is implemented in the device 100, any of the specific configurations or modes of anti-bradycardia pacing therapy which may be implemented on the pacing unit 102, and any of the specific sensing configurations required for operating the CCM unit 108, including but not limited to, the sensing methods and configurations disclosed in the PCT publications to Ben Haim et al. and in the co-pending U.S. patent application Ser. Nos. 09/276,460, 09/328,068 and 09/338,649 to Mika et al. referenced hereinabove, and in the corresponding PCT applications.

In order to prevent or at least to reduce the probability of the misclassification and the resulting delay or failure of the proper application of antiarrhythmic therapy, the device 100 is adapted to use the threshold based method to disable the delivery of CCM signals to the heart when the detected heart rate exceeds a certain threshold as is disclosed in detail for the device 51 of FIG. 3.

Thus, in accordance with a preferred embodiment of the present invention, the device 100 continuously determines the heart rate and classifies the heart rate, in accordance with any sensing, detecting, and anti-arrhythmic heart rate classification methods or algorithms known in the art. Simultaneously, the CCM unit 108 and the microprocessor unit 106 operate to detect the need for CCM therapy and to control the delivery of CCM signals to the heart in accordance with any of the methods of CCM signal delivery known in the art or disclosed in any of the above referenced published or co-pending patent applications disclosed hereinabove. If the heart rate exceeds a certain threshold level, this heart rate is classified as a suspected tachy-arrhythmia and the microprocessor 106 disables the delivery of CCM signals to the heart within the CCM signal free period, disclosed hereinabove.

Typically, the heart rate is determined by determining the R—R interval as is known in the art, but other methods may also be used.

The threshold level value for determining the suspected tachy-arrhythmia is preferably individually adapted to each patient and then set by programming it into the memory unit(s) 124 by communicating it telemetrically or non-telemetrically to the device 100 as is known in the art. This individual determination and setting of the value of the heart rate threshold level for suspected tachy-arrhythmia has the advantage of enabling to fine-tune the operation of the device 100 such as to find an appropriate balance between minimizing undesired masking, delayed detection, or non-detection of therapy requiring tachy-arrhythmic episodes due to use of the above disclosed refractory period and maximizing the upper heart rate level at which CCM therapy may still be delivered to the heart.

The precise value of the acceptable threshold level may be influenced, inter alia, by the type of cardiac disorder of the patient, the presence or absence of cardio-therapeutic drugs used by the patient, and data collected in the same patient under normal cardiac conditions, SVT conditions, VT conditions and possibly VF conditions. The setting of the threshold value may have to be performed by a physician or cardio-physiologist based on study of such patient conditions and on the degree of desired CCM modification for that patient.

Typically, an exemplary non-limiting value for the heart rate threshold level is 150 heart beats per minute. However, other larger or smaller threshold level values may also be used, according to the individual patient cardiac conditions.

The disabling of the delivery of CCM signals is performed by the microprocessor unit 106 by sending appropriate control signal or signals to the CCM unit 108. The device 100 then continues to determine the heart rate within this CCM signal free period in the absence of CCM signal delivery. The microprocessor 106 of the device 100 analyzes and classifies the heart rate in accordance with the classification criteria based on the detection signal data which are sent from one or more of the detecting units 116 to the microprocessor unit 106 during the CCM signal free period. The microprocessor 106 of the device 100 then determines whether any type of anti-arrhythmia therapy is to be delivered to the heart based on the classification of the heart rate obtained in the CCM free period.

If the classification of the heart rate resulting from the processing of the detection data obtained in the CCM free period indicates the need to deliver any type of anti-arrhythmic therapy, the microprocessor 106 continues the disabling of CCM signal delivery and initiates the delivery of the required antiarrhythmic therapy by sending appropriate control signals to the anti-tachyarrhythmic unit 118, and continues to deliver any indicated antiarrhythmic therapy and to determine and classify the heart rate as is known in the art until the anti-arrhythmic therapy is terminated. If the anti-arrhythmic therapy is terminated by the microprocessor 106, the microprocessor 106 enables the delivery of CCM signals to the heart by sending a suitable enabling control signal to the CCM unit 108.

If the classification of the heart rate obtained in the CCM free period does not indicates a need to deliver any type of anti-tachyarrhythmic therapy, the microprocessor 106 enables the delivery of CCM signals to the heart by sending a suitable enabling control signal to the CCM unit 108.

Similar to the method disclosed for the device 51 of FIG. 3, the anti-tachyarrhythmia detection and classification program, sub-routine or algorithm operative on the microprocessor unit 106 takes priority over the CCM delivery control program, subroutine or algorithm which is also operative on the microprocessor unit 106, enabling it to override, interrupt, or disable the CCM signal delivery even under conditions in which the delivery of CCM signals is called for by the CCM delivery control program to modify cardiac contractility and or cardiac output.

Preferably, but not necessarily, the detection of bradycardia and the delivery of anti-bradycardia pacing therapy is performed by pacing programs, subroutines or algorithms which are operative on the microprocessor 106 as is known in the art and disclosed hereinabove.

It is noted that, if the sensing unit(s) 112 include a plurality of sensing units operative for providing sensing of signals at different sites of the heart, the sensing units 112 may be, but need not necessarily be, identical units and may differ from each other to be adapted for sensing specific signals.

Similarly if the detecting units 116 include a plurality of detecting units operative for providing event detecting for signals sensed at different sites of the heart, the detecting units 116 may be, but need not necessarily be, identical units and may differ from each other to be adapted for detection of specific sensed and amplified signals.

it is noted that the CCM devices 30, 51 and 100 of FIGS. 2,3 and 4 respectively, may be adapted for acute implantation in a patient for short term patient monitoring and therapy treatment such as for temporary use in intensive care hospitalized patient's. Alternatively, the CCM devices 30, 51 and 100 of FIGS. 2,3 and 4 respectively, may be adapted for used as implantable devices for chronic implantation.

Novel Anti-Arrhythmic Effect of CCM Signals

The use of CCM therapy is mainly directed to modulating the contractility of the heart as is known in the art and disclosed hereinabove. For example, CCM signals may be used for modulating myocardial contractility to controllably modulate the cardiac output. Thus, CCM therapy may be used, inter alia, to increase cardiac output in CHF patients or other types of cardiac patients without increasing the heart rate.

While evaluating the results of clinical tests of CCM therapy in human patients, originally designed for evaluating the efficacy and safety of the CCM therapy (which is also known in the art as ETC therapy), the inventors of the present invention have noticed an unexpected anti-arrhythmic effect of CCM therapy in the patients.

Experiments Demonstrating a Novel Anti-Arrhythmic Effects of CCM Therapy

The data was gathered in 21 human patients with diagnosed CHF, prior to, during and following the application of CCM therapy.

The CCM therapy was transvenously applied to the patients. In each of the patients included in the study, a CARDIMA™ REVELATION™ microcatheter, product No. 01-082007, commercially available from CARDIMA Inc., CA, U.S.A., was introduced through the coronary sinus (CS) into the great cardiac vein (GCV) and positioned in a branch of the GCV. In part of the patients, the microcatheter was positioned in the posterior branch of the GCV. In other patients, the microcatheter was positioned in the lateral branch of the GCV, and in other patients the microcatheter was positioned in the anterior branch of the GCV. This microcatheter includes eight coil electrodes which are equally spaced along the microcatheter and one distal tip electrode that was not used in the study. The microcatheter was used for the delivery of the CCM signals through a selected pair of electrodes located on the microcatheter. Typically, the CCM signals where delivered to the heart through a pair of electrodes selected from the six electrodes closest to the tip of the microcatheter. The CCM signals (also referred to as ETC signals herein) were delivered using the method based on ventricular triggering as disclosed in co-pending U.S. patent application Ser. No. 09/276,460 to Mika et al., and in the corresponding PCT applications.

The CCM signal used in all of the patients was a square wave with a delay of 20–90 milliseconds from the triggering event, a pulse duration of 20–40 milliseconds, and a current amplitude of 6–15 milliamperes. Each patient was given CCM therapy for a session lasting about an hour, the therapy session consisted of several periods of CCM signal delivery each lasting approximately 2–20 minutes. These periods of CCM signal delivery were separated from each other by intermission time periods of about 3–10 minutes. During the intermission time periods no CCM signals were delivered to the heart of the patients.

The CCM device used for delivering the CCM signals was also capable of pacing. Each of the patients also had two inserted electrophysiology (EP) diagnostic catheters, one diagnostic catheter was placed in the patient's right atrium and the other diagnostic catheter was placed in the patient's right ventricle. The catheters were commercial electrophysiology catheters such as, the EP diagnostic catheter, catalogue No. F6-QS-010-PS, commercially available from Cordis Webster Incorporated CA, USA,. All the patients were paced throughout the CCM therapy session, except for one patient in which the pacing was stopped for a portion of the CCM therapy session. When the F6-QS-010-PS EP diagnostic catheter was used for pacing, the tip electrode and the first (most distal) ring electrode were used for bipolar pacing.

The EP diagnostic catheters were used for sensing and for pacing, as is known in the art. All the patients were paced using a DDD pacing mode. Some of the patients were paced using a DDD bi-ventricular mode. In these patients, bi-ventricular pacing was carried out using the CARDIMA™ microcatheter to pace the left ventricle. When the CARDIMA™ microcatheter was used for left ventricular pacing the pacing was bipolar pacing and was applied to the heart transvenously through the same coil electrode pair that was selected for delivering the CCM signals to the patient.

The following data were digitized, recorded, and stored as digital data on the hard disk of a computer for each of the CCM therapy session of each patient: the sensed intracardiac electrogram signals (IEGM) in left ventricle (LV), the electrocardiogram signal (ECG lead II), the pacing pulses in each of the relevant pacing electrodes, and the left ventricular pressure (LVP) as determined by a MILLAR® Mikro-Tip® catheter transducer Model SPC-370, commercially available from MILLAR INSTRUMENTS Inc, TX, USA.

The pressure catheter was inserted into the LV of each patient using standard femoral artery insertion procedures. Another pressure catheter was used to record the aortic pressure. The data recorded from each patient was stored in one or more data files.

When the results of the experiments where evaluated, ectopic beats (EB's) were defined based on the duration of the median R—R interval. For each recorded data file, the R—R intervals were determined. The median value of the R—R interval was found for each data file by taking the median of all the computed R—R intervals for all the beat cycles within that data file. All the heart beats of the data file where then classified as ectopic beats or normal beats. Any R—R interval that deviated by more than ±10% from the median R—R interval of that data file was classified as an ectopic beat. The remaining R—R intervals in the data file were classified as normal beats.

For data analysis, all the classified beats from all the sessions of all the patients were pooled and divided into two groups, a "test" group including all the beats which occurred in the "test periods" and a "control" group including all the beats which occurred in the "control periods". The test periods were defined as a sequence of heart beats in which CCM signals were delivered, starting with the third consecutive heart beat in which a CCM signal was delivered and ending with the last heart beat in which a CCM signal was delivered (the last heart beat is included within the test period). The control period included all the other heart beats in the experiments which were not included in the test periods. A third group, referred to as the "before CCM" periods group, included all the heart beats occurring during the intermission time periods between the periods of CCM signal delivery applications, with the additional condition that they occurred within the last 60 seconds or less of the intermission time period immediately preceding the beginning of the next CCM signal delivery period. This is deemed to be the time within the intermission time period that is least subject to the effects, if any, of the previous activation of CCM signals in the experiments.

The results of the analysis are given in TABLE 1 and TABLE 2.

In TABLE 1 and TABLE 2, the first column indicates the condition group, the second column indicates the total number of beats in the group, the third column indicates the total number of ectopic beats in the group, the fourth column indicates the number of ectopic beats per 1000 beats, and the fifth column indicates the computed 95% confidence level (95% CI).

The sums indicated in the fourth row (labeled by the word "sum") of the second column of each of TABLE 1 and TABLE 2, represent the sum of the total number of beats of the first and second rows of the respective table. As defined hereinabove, the "before CCM" periods are part of the "control period", and are therefore not included in the "sum" of the fourth row to avoid double counting.

TABLE 1

| ALL patients | Total Beat No. | Total EB's | Rate (EB's/ 1000 beats) | 95% CI |
|---|---|---|---|---|
| Rate of ectopic beats during "Control period"; | 60,239 | 2,851 | 47.32 | ±1.70 |
| Rate of ectopic beats during "test periods" | 53,611 | 2,170 | 40.48 | ±1.67 |
| Rate of ectopic beats during "before CCM" periods: | 19,019 | 902 | 47.42 | ±3.02 |
| Sum | 113,850 | | | |

The results of TABLE 1 show that there was a significant reduction of 16.9% (Calculated as % reduction=(47.32−40.48)/40.48×100) in the rate of ectopic beats during the delivery of CCM signals to the heart (referred to as the "test period" in TABLES 1 and 2).

The results of the data from all the patients which were not bi-ventricularly paced were pooled and analyzed separately as disclosed hereinabove. The results which are shown in TABLE 2, show a similar reduction in EB rate compared to control.

TABLE 2

| Non-Biventricular patients | Total beats | Total EB's | Rate (EB's/ 1000 beats) | 95% CI |
|---|---|---|---|---|
| Rate of ectopic beats during "Control period" | 46,755 | 2,302 | 49.24 | ±1.96 |
| Rate of ectopic beats during "test periods"; | 42,535 | 1,735 | 40.79 | ±1.88 |
| Rate of ectopic beats during "before CCM" periods: | 15,206 | 718 | 47.22 | ±3.37 |
| Sum | 89,290 | | | |

The results of TABLE 2 indicate that there is a significant ($p<0.001$) reduction in ectopic beats count. (CI 95%:9.44–19.50) in periods of CCM signal delivery (the test periods).

The inventors of the present invention have therefore noted that, these unexpected experimental results indicate that besides the known use of CCM signals for cardiac contractility modulation and cardiac output modulation, the application of CCM signals to the heart may also be used as a therapeutic treatment for tachyarrhythmic conditions.

Prior art anti-tachyarrhythmia devices, may use the following method to detect and treat tachyarrhythmias, depolarization events are sensed and detected, the cardiac rhythm is then classified as belonging to a "group" such as for example, slow VT, fast VT, VF the device then determines what is the appropriate therapy type based on the results of the rhythm classification and on past therapy results. For example, if ATP was attempted and failed for treating fast VT, cardioversion may be attempted. After the arrhythmia type is determined based on the classification, the selected therapy type is applied to the heart.

Different ICD devices are distinguished, inter alia, by the classification methods which they use for arrhythmia classification. Most devices use criteria, which are known in the art as "stability" and "onset", to distinguish different kinds of arrhythmia once a basic rate computation led to the detection of arrhythmia. Typically, arrhythmia detection methods are based on counting depolarization events. However, different devices may use different arrhythmia detection methods. During arrhythmia, depolarization events tend to be smaller in amplitude and therefor harder to detect. This is taken into account by different rate calculating algorithms differently. Generally, the intervals between detected depolarization events are examined. One may look at intervals between events falling within a certain time period, and take a certain percentage of the shortest ones to determine whether they are shorter than a certain threshold value. This is known in the art as the "X out of Y criterion". Alternatively, the device may compute the average of the intervals within a time period or of a subgroup of the intervals. Some examples of tachy-arrhythmia detection methods are disclosed by Stan M. Bach et al. in Chapter 15 titled "TACHYARRHYTHMIA DETECTION", pp. 303–323, of the book titled "IMPLANTABLE CARDIOVERTER DEFIBRILLATOR THERAPY: THE ENGINEERING-CLINICAL INTERFACE", Eds. Mark W. Kroll and Michael H. Lehmann, Kluwer Academic Publishers, USA, 1997, incorporated herein by reference. However, other arrhythmia detection methods are also known in the art, including but not limited to methods using morphological signal analysis. It is noted that many other methods for detecting tachy-arrhythmias are known in the art, and that all such suitable currently known tachy-arrhythmia detection methods are intended to be included within the scope of the present invention.

Stability of the heart rate and the speed of onset of the arrhythmia are indicators which are often used to distinguish different types of arrhythmia as is well known in the art.

It is desirable to detect the onset of arrhythmia as early as possible, in order to have enough time to apply the types of anti-tachyarrhythmic therapy that are less painful to the patient, less energy consuming, and less hazardous, such as ATP, while they might still have effect. For example, ATP has very little or no effect in treating VF, but may have good results in treating slow VT. Usually, heart rate is used to classify the arrhythmia in order to decide which therapy type to try first. Speed of therapy application is important in order for the therapy to be effective before the heart deteriorates from slow arrhythmia to faster arrhythmia, and to prevent the heart from becoming more ischemic, until asystole or clinical death results if no treatment is timely applied. Stability and onset criteria are used to distinguish VT from SVT to decide whether treatment is necessary, and if so, which treatment type to apply. Therefore, many anti-tachyarrhythmic devices monitor the rate and onset of an arrhythmia.

It is noted that a tachyarrhythmia is classified as a sequence of ectopic beats by the classification method that was used in the analysis of the experimental data presented in TABLE 1 and TABLE 2. Thus, the "ectopic beat" (EB's) class in the experiments included doublet and triplet ectopic events. It is also noted that generally, tachy-arrhythmias start as a sequence of ectopic beats which evolves into an arrhythmic sequence.

Thus, in accordance with a preferred embodiment of the present invention, an anti-arrhythmia device is disclosed which is adapted to include the delivery of CCM signals to the heart in response to the detection of a cardiac tachyarrhythmia. Such a device may utilize the above disclosed unexpected effect of CCM signal delivery to reduce the rate of occurrence of ectopic beats as a therapeutic means to stop or diminish the detected tachyarrhythmia.

Furthermore, the present invention discloses a new method for operating an anti-arrhythmic device having CCM signal delivery capabilities. The method comprises the controlled application of CCM signal delivery in response to the detection of a tachyarrhythmia by the device.

The delivery of CCM signals as means for achieving anti-arrhythmia therapy may be performed using CCM delivery timing methods and devices as disclosed in detail in the above referenced co-pending U.S. patent applications Ser. Nos. 09/276,460, 09/328,068 and 09/338,649 to Mika et al., and in the corresponding PCT applications. The CCM signal parameters may be the square current pulse parameters disclosed hereinabove in the clinical experiments performed in the CHF patients, but may also be any other suitable CCM signal parameters which are effective for treating tachyarrhythmias. Various different forms of CCM signals are known in the art and disclosed in the above referenced PCT publications to Ben Haim et al., having International Publication Numbers WO 97/25098, WO 98/10828, WO 98/10829, WO 98/10830, WO 98/10831, and WO 98/10832. These CCM signal forms (also referred to as ETC signal forms) may be useful for CCM anti-arrhythmia therapy.

In accordance with one preferred embodiment of the present invention, the method for delivering CCM signals to the heart in order to treat arrhythmia includes methods of detection of arrhythmia as is known in the art. Any of the methods including sensing, event detection and tachy-arrhythmia classification algorithms may be used to detect arrhythmia. For example, PVC detection as achieved by using the sequential activation of ventricles following the atria in every heart beat, as is well known in the art, may also be used as a method to detect arrhythmia.

The method for delivering CCM signals to the heart in order to treat arrhythmia further includes calculation of the prevalence of arrhythmia at any given time. In accordance with one preferred embodiment of the present invention, calculation of the prevalence of arrhythmia at any given time consists of counting the number of detected arrhythmia episodes in a given period of time.

Different arrhythmia types may be counted separately when calculating the prevalence of arrhythmia. Alternatively or additionally, different kinds of arrhythmia may be pooled together for calculating the prevalence of arrhythmia. For example, the prevalence of any length of PVC run (including a single PVC, PVC couplets, PVC triplets and the like) may be calculated as the sum of all such arrhythmic episodes occurring in a given period of time.

The calculated prevalence of arrhythmia is compared to a value representing the level of prevalence of arrhythmia that requires CCM therapy initiation. The level of prevalence of arrhythmia that requires CCM therapy initiation is, preferably, set for each patient separately based on the arrhythmic history and prognosis of the patient as may be obtained and evaluated by a physician or cardiologist from examination of the patients ECG trace, other suitable available types of recorded electrical cardiac activity such as, but not limited to, IEGM recordings, and recorded medical history.

Once the level of prevalence of arrhythmia required for the initiation of CCM therapy is exceeded by the actual calculated prevalence of arrhythmia. CCM signal delivery is initiated for a first period of CCM therapy. The first period of CCM therapy includes a number of heart beats which may be a preset number of heart beats or may be dependent upon the type or other parameters of the detected arrhythmia, or upon the calculated prevalence of arrhythmia. Additionally, the parameters of the CCM signals delivered to the heart may be preset or may also be determined by the type of the detected arrhythmia or by other parameters of the detected arrhythmia, or by the calculated prevalence of arrhythmia.

During the first period of CCM therapy, arrhythmia detection is performed in the presence of the delivered CCM signals, as disclosed in detail hereinabove. Upon detection of arrhythmia during the application of CCM therapy, CCM signal delivery may be stopped so that another type of anti-arrhythmic therapy may be employed, depending upon the nature and parameters of the detected arrhythmia. For example, CCM signal delivery may be stopped if VF is detected during CCM delivery, in order to deliver a defibrillating shock. Alternatively, parameters relating to CCM delivery, such as, but not limited to, the waveform, duration, amplitude or polarity of the CCM signals, may be modified according to parameters relating to the arrhythmia detected.

Once the first period of CCM therapy ends, detection of arrhythmia continues and CCM therapy may be employed again, depending on the arrhythmia detected. For example, a decline in the prevalence of arrhythmia during or immediately following the application of CCM therapy, followed by an increase of arrhythmia prevalence once CCM therapy is stopped, may lead to re-initiation of CCM therapy using the same CCM signal parameters as in the first period of CCM therapy. However, different parameters such as, but not limited to, duration, waveform, amplitude and polarity of the CCM signals may also be used in the second period of CCM therapy. For example, a longer duration of CCM therapy may be used for the second period of CCM delivery.

In accordance with another embodiment of the present invention, the method for delivering CCM signals to the heart in order to treat arrhythmia includes methods of detecting possible indications of arrhythmia as are known in the art. For example, T-wave alternans may serve as an indicator of increased risk of arrhythmia, as disclosed by Richard et al. in an article titled "ELECTROPHYSIOLOGICAL BASIS FOR T WAVE ALTERNANS AS AN INDEX OF VULNERABILITY TO VENTRICULAR FIBRILLATION" published in the Journal of Cardiovascular Electrophysiology, Vol. 5, pp. 445–461 (1994) and incorporated herein by reference.

Once the indications of arrhythmia exceed a certain level, which may be a preset level or may be dependent upon the type or other parameters of the indications of arrhythmia detected, CCM therapy may be initiated for a first period of CCM therapy. During the first period of CCM therapy or following the first period of CCM therapy, depending on the type of arrhythmia indication detected, the CCM signal parameters, such as, but not limited to, the duration, waveform, amplitude and polarity of the CCM signal, may be altered. Additionally or alternatively, another period of CCM therapy may be employed based on the arrhythmia indications detected following a period of CCM therapy.

Preferably, the detection of arrhythmia and of indications of arrhythmia is performed simultaneously, and the delivery of CCM therapy is initiated either if an arrhythmia is detected, as disclosed hereinabove, or if arrhythmia indications are detected, as disclosed hereinabove.

Reference is now made to FIGS. 5–8 which are schematic diagrams illustrating different preferred embodiments of the anti-arrhythmic device of the present invention which are adapted for delivering CCM signals having anti arrhythmic effects to the heart.

Figure 5:
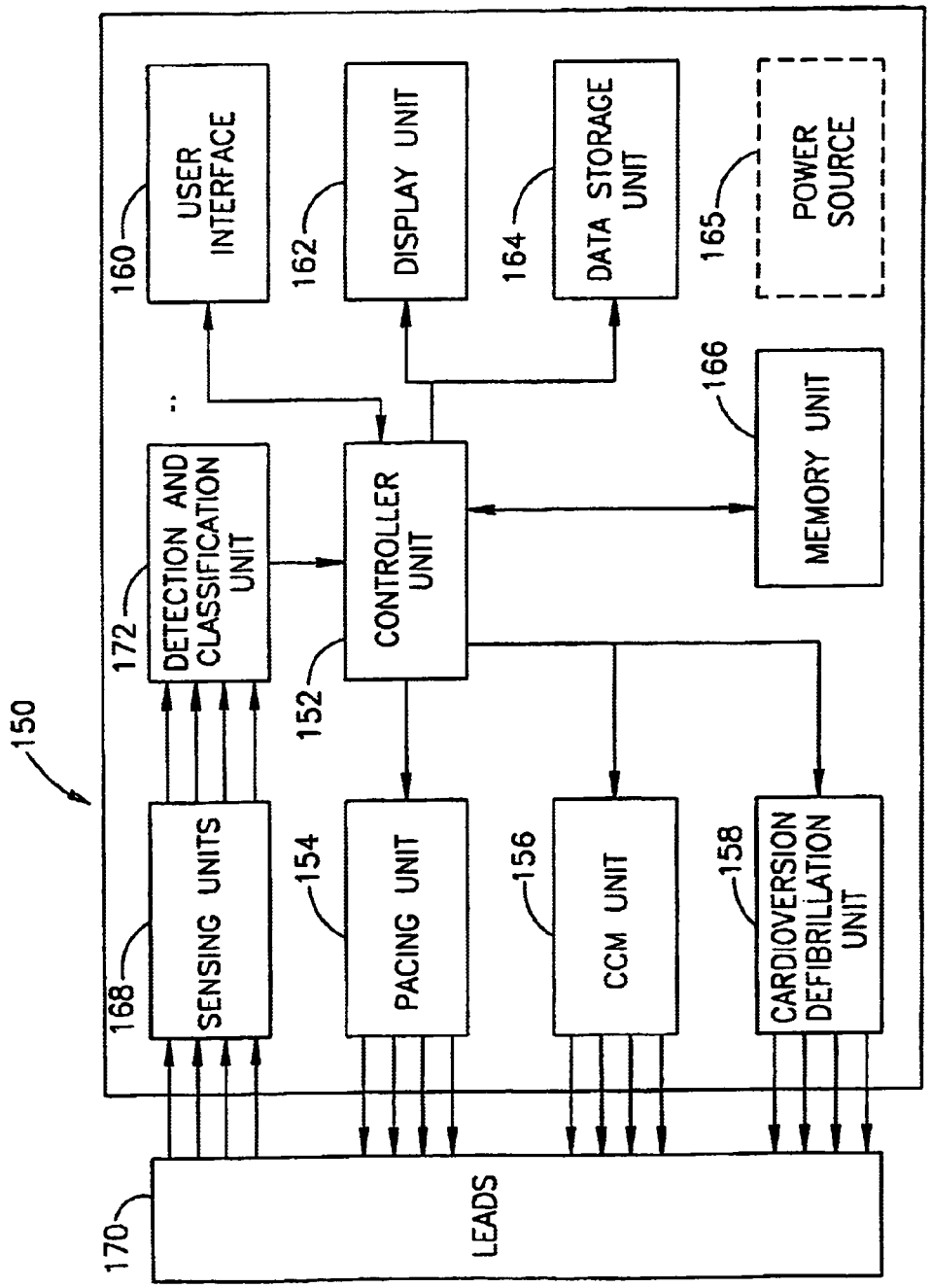
FIGS. 5–8 are schematic diagrams illustrating different implantable and non-implantable preferred embodiments of the anti-arrhythmic device of the present invention which are adapted for delivering CCM signals having anti arrhythmic effects to the heart.

FIG. 5 illustrates an external anti-arrhythmic device 150. The device 150 includes a controller unit 152. The controller unit 152 may be any type of controller unit such as a micro-controller, a microprocessor, or the like. The controller unit 152 is operatively connected to a pacing unit 154, a CCM unit 156 and a cardioversion/defibrillation unit 158 for controlling the operation thereof. The controller 152 is also connected to a user interface 160 for providing output to a user and for receiving commands from the user. The user interface may be any type of user interface, such as but not limited to, a keyboard, a light pen, a touch-pad a pointing device, a touch sensitive display screen or any combination thereof. The controller 152 is also connected to a display unit 162 for providing visual output to the user of the device 150, such as but not limited to graphic output, alphanumeric output, graphic signs and icons, and any combination thereof. The display unit may be any type of display unit known in the art, such as a cathode ray tube display, a liquid crystal display, a plasma display, a photoluminescent display, and the like.

The controller 152 is also connected to a data storage unit 164 for storing and retrieving data and information by the user of the device 151 and by the controller unit 152, such as but not limited to, a magnetic disc storage device, a removable magnetic media storage device, a solid state memory storage device, an opto-magnetic storage device, an optical storage device, or any other type of device for storing digital information, or other data types, known in the art.

The controller 152 is also suitably connected to a memory unit 166 for storing and retrieving data and information by the controller unit 152. The memory unit 166 may include one or more memory devices (not shown) for storing and retrieving data. The memory unit 166 may include any read-only memory devices and/or read-write memory devices for storage and retrieval of data, as is known in the art.

The device 150 is connectable to one or more leads 170 as is known in the art, the leads may be any type of suitable leads which are known in the art and which include one or more electrodes for pacing, sensing, delivering cardioversion/defibrillation therapy and delivering CCM signals to the heart. The leads 170 may be implantable or temporary leads. The device 150 further includes one or more sensing units 168. The sensing units 168 are connectable to one or more electrodes (not shown) included in the leads 170. The sensing units are adapted for sensing electrical depolarization events of the heart as is well known in the art. The sensing units may also includes amplification circuitry (not shown) for amplifying the sensed signals as is known in the art. The sensing electrodes (not shown) may be disposed at or about a plurality of cardiac sites. For example, in accordance with one non-limiting example, the sensing units 168 are connected to sensing electrodes (not shown) disposed at or about the left atrium, the right ventricle and the left ventricle of the heart.

The device 150 further includes a detection and classification unit 172 which is operatively connected to the sensing units 162 and to the controller unit 152, and is operative to detect depolarization events in the electrical signals sensed by the sensing units 168. The detection and classification unit 172 is also operative to classify the heart rate based on the detected events in order to detect various types of arrhythmias as is known in the art. The detection and classification unit 172 may be any detection and classification unit known in the art and suitable for classifying arrhythmias.

The pacing unit 154 may be operatively connected to one or more electrodes (not shown) of the leads 170. The electrodes may be dedicated pacing electrodes or any other type of electrode which may also be used for sensing, delivering CCM therapy, or delivering cardioversion/defibrillation therapy. The pacing unit 154 may be adapted to deliver anti-bradycardia pacing therapy as is well known in the art. In accordance with one non-limiting example, the pacing unit is operatively connected to pacing electrodes disposed at or about the right atrium (RA) and the right ventricle (RV) and may be used for uni-ventricular or biventricular pacing as is known in the art. Other pacing forms or electrodes configurations may also be used, and are included within the scope of the present invention.

It is noted that the device 150 may also include one or more timing units (not shown) connected to the controller unit 152 or to the pacing unit 154 for providing timing signals (clocking signals) to the controller unit 152 or to the pacing unit 154.

The device 150 also includes a power source 165 for providing power to the various components of the device 150. The power source 165 is suitably operatively connected (connections not shown for the sake of clarity of illustration) to provide electrical energy the components of the device 150 as is known in the art. The power source 165 may be an electrochemical cell or a battery (primary or rechargeable), or the like but may be any other suitable power source for providing electrical power which is known in the art. It is noted that while the power source 165 is shown as included within the device 150, the power source 165 may be also disposed externally to the device 150. For example, the power source 165 may be a power source such as, but not limited to, a conditioned or regulated DC or AC power supply, operatively connected to the mains power supply (not shown) as is known in the art.

The CCM unit 156 may be used for applying CCM signals to the heart as is known in the art and disclosed in detail hereinabove. The application of the CCM signals is performed through one or more electrodes or electrode pairs which are within the leads 170. The electrodes may be disposed at or about one or more sites in the heart, such as but not limited to, one or more parts of the left ventricle.

The controller 152 controls the delivery of CCM signals to the heart as disclosed hereinabove, using timing methods as disclosed in the above referenced co-pending US patent applications to Mika et al., and in the corresponding PCT applications. The CCM signals may be used for modifying the cardiac contractility and the cardiac output as is disclosed hereinabove and known in the art. Additionally, the controller 152 may also control the CCM unit to deliver CCM signals as therapy for a detected tachy-arrhythmia which is detected by the detection and classification unit 172 using any suitable detection and classification methods known in the art or disclosed hereinabove. To initiate a CCM therapy period as disclosed hereinabove, the controller 152 may initiate CCM therapy by controlling the CCM unit 156 to deliver CCM signals to the heart through the appropriate electrodes (not shown) of the leads 170. The method of delivery of the CCM signals as anti-arrhythmia therapy is disclosed in detail hereinabove.

The cardioversion/defibrillation unit 158 of the device 150 may be any cardioversion/defibrillation unit known in the art and disclosed hereinabove. The cardioversion/defibrillation unit 158 may operate to deliver cardioversion therapy and or defibrillation shock therapy to the heart through suitable cardioversion and/or defibrillation electrodes disposed in or about the heart, as is known in the art. The electrodes (not shown) used for delivering cardioversion and/or defibrillation therapy may be epicardial electrodes, transvenous electrodes, intracardiac electrodes, or any other type of suitable electrodes known in the art.

If the tachy-arrhythmia does not respond well to the anti-arrhythmic CCM therapy, the controller 152 may control the cardioversion/defibrillation unit 158 to deliver other suitable types of anti-tachycardia therapy such as for example, cardioversion therapy or defibrillation shock therapy as disclosed hereinabove.

Typically, the device 150 is an external non-implanted device which may be used for patient supporting and therapy in cardiac patients such as cardiac patients in intensive care unit after cardiac surgery, or a heart condition. In operation, the device 150 is suitably connected to the appropriate leads 170 which are inserted into the patient and may be used to apply different forms of cardiac therapy as disclosed hereinabove as well as td record and/or monitor the patient's cardiac conditions and the effects of different therapy types on the heart. The device may also be used in data recording sessions in the patient which may be used for recording data and for processing, analyzing and displaying data. The data may be used by a physician or cardiologist for determining various thresholds and parameter values of the pacing sensing, CCM delivery (including CCM alert window parameters), and cardioversion or defibrillation parameters.

Figure 6:
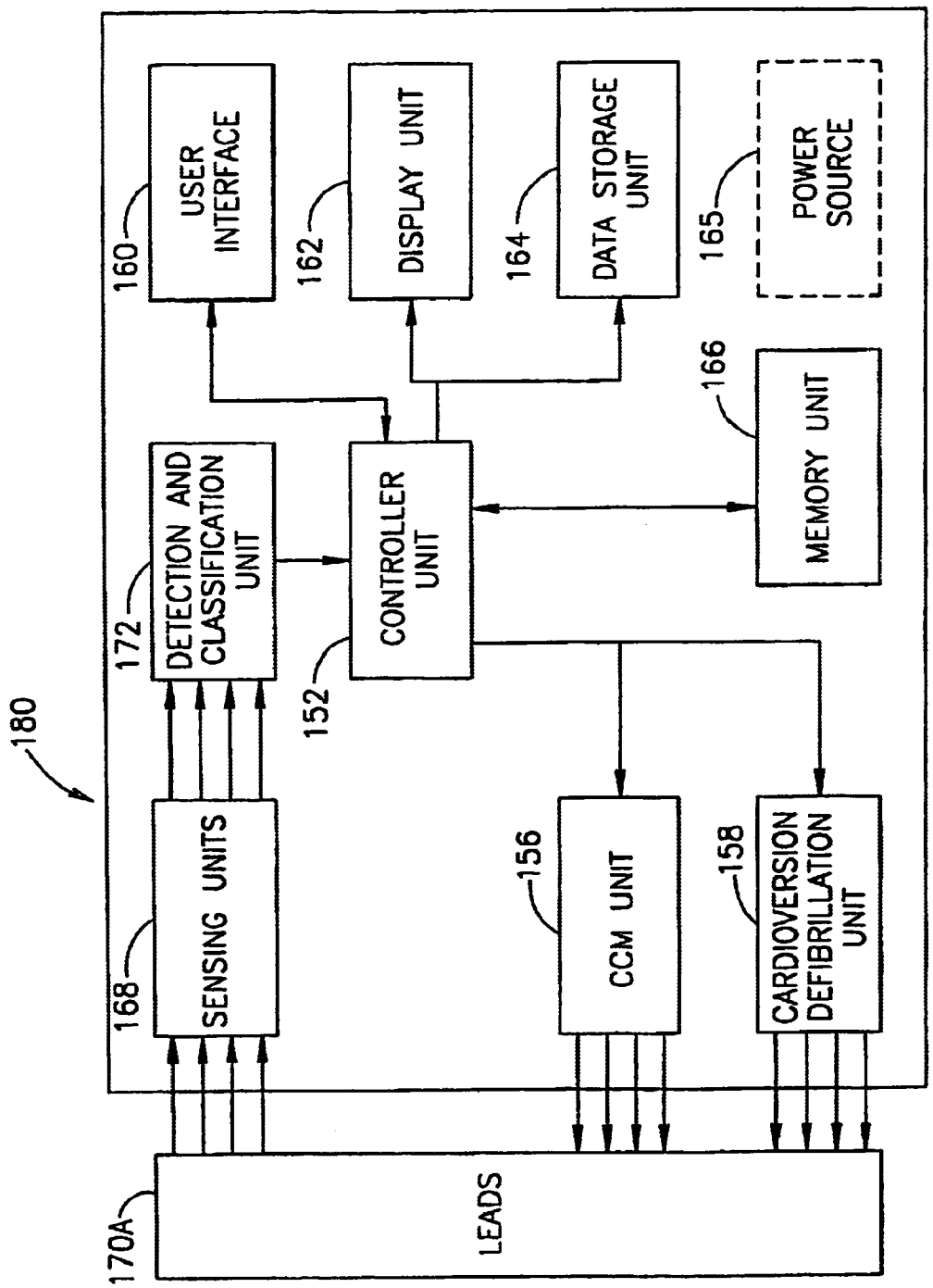

It is noted that the external device 150 may also be implemented without a pacing unit FIG. 6 illustrates such an external anti-arrhythmic device 180 which does not include a pacing unit. The device 180 is similar to the device 150, except that the pacing unit 154 is absent in the device 180. Thus, the device 180 does not provide pacing capabilities and therefore cannot be used for providing anti-bradycardia pacing therapy to the patient. The operation and use of the device 180 for detecting tachy-arrhythmia and for providing various types of anti-arrhythmic therapy types including, inter alia, CCM signal anti-arrhythmic therapy is similar to the operation and use of the device 150 as disclosed in detail hereinabove. The device 180 may be useful for treating patients who are not in need of pacing therapy. The device 160 is connectable to leads 170A which may be identical to the leads 170 of the device 150, but may also be different from leads 170 of the device 150. Since the device 160 does not include a pacing unit, there is no need for pacing electrodes therefore at least some of the leads 170A may be leads including a smaller number of electrodes. However, frequently, the pacing unit and the sensing units may use the same electrodes for sensing and pacing, therefore, the leads 170A may be similar to the leads 170, except that no pacing is performed through the sensing electrodes.

Figure 7:
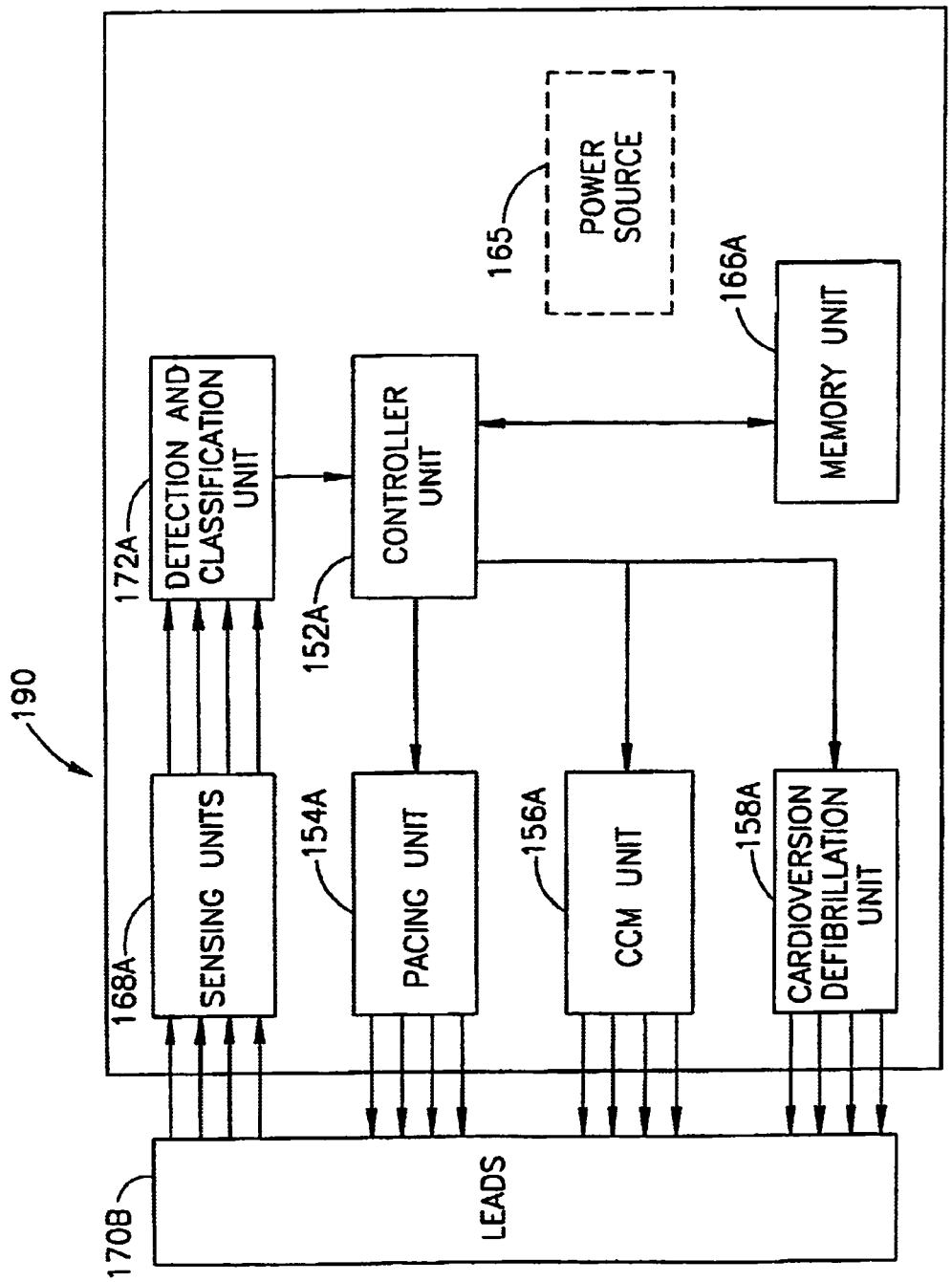

It is further noted that, implantable devices with anti-arrhythmic CCM therapy capabilities may also be constructed. FIG. 7 illustrates an implantable anti-arrhythmic device 190 having anti-arrhythmic CCM therapy capabilities. The device 190 is similar in operation to the device 150 of FIG. 5 except that the device 190 does not include the user interface 160, the display unit 162 and the data storage unit 164 which are included in the external device 150. The implantable device 190 is adapted for being chronically implanted in a cardiac patient. Therefore, the device 190 includes a pacing unit 154A, sensing units 168A, a CCM unit 156A, a cardiovertion/defibrillation unit 158A, a controller unit 152A, a memory unit 166A, and a detection and classification unit 172A which are functionally and operatively similar to the pacing unit 154, the sensing units 168, the CCM unit 156, the cardiovertion/defibrillation unit 158, the controller unit 152, the memory unit 166, and the detection and classification unit 172, respectively, of the device 150 of FIG. 5. However, the pacing unit 154A, the sensing units 168A, the CCM unit 156A, the cardiovertion/defibrillation unit 158A, the controller unit 152A, the memory unit 166A, and the detection and classification unit 172A may be miniaturized to adapt them for operating in an implanted device as is known in the art. The device 190 is operatively connectable to leads 170B. The leads 1.708 may be similar to the leads 170 of FIG. 5, except that the leads 170B must be implantable leads while the leads 170 may be implantable leads or temporary insertable leads.

It is noted that the implantable device 190 may also include a telemetry unit (not shown) operatively connected to the controller 152A for telemetrically communicating with a telemetry transceiver (not shown) disposed outside the patient as is known in the art. The telemetry unit (if included in the device) may be used to program data and instructions or commands into the memory unit 166A for wirelessly changing the operating programs of the device 190 and for telemetrically transmitting data related to the patient's cardiac condition to the external telemetry transceiver for patient monitoring and for data analysis.

It is further noted that the implantable device 190 may also include one or more timer units (not shown) operatively connected to the controller unit 152A for providing timing or clock signals thereto.

Figure 8:
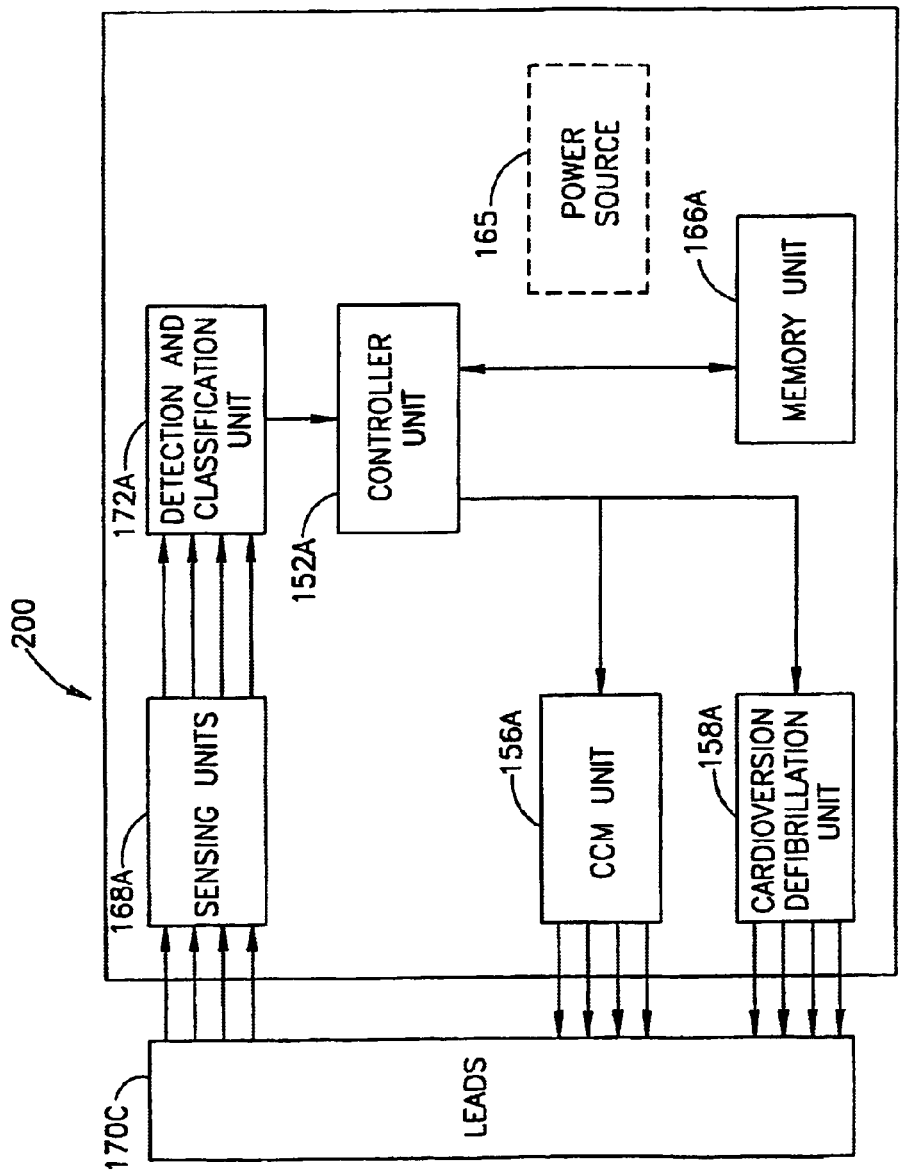

FIG. 8 illustrates an implantable anti-arrhythmic device 200 which does not include a pacing unit. The device 200 is similar to the device 190 of FIG. 7, except that the pacing unit 154A is not included in the device 200. Thus, the device 200 does not provide pacing capabilities and therefore cannot be used for providing anti-bradycardia pacing therapy to the patient. The operation and use of the device 200 for detecting tachy-arrhythmia and for providing various types of anti-arrhythmic therapy types including, inter alia, CCM signal anti-arrhythmic therapy is as disclosed in detail hereinabove. The device 200 may be useful for treating patients who are not in need of pacing therapy. The device 200 is connectable to leads 170C which may be implantable leads similar, with respect to electrode number and configuration, to the leads 170A or 170B of the devices 180 and 190, respectively, but may also be different from leads 170A and 170B. Since the device 200 does not include a pacing unit, there is no need for pacing electrodes, therefore at least some of the leads 170C may be leads including a smaller number of electrodes than the number of electrodes included in the leads 170B of the implantable device 190. However, frequently, the pacing unit and the sensing units may use the same electrodes for sensing and pacing. Thus, the leads 170C may be similar, with respect to electrode number and configuration, to the leads 170B, except that no pacing is performed through the sensing electrodes of the leads when they are connected to the device 200. The leads 170C may be implantable leads adapted to being chronically implanted.

Each of the implantable devices 100, 190 and 200 also includes a power source 165 for providing power to the various components of the devices 100, 190 and 200, respectively. The power source 165 is suitably operatively connected (connections not shown for the sake of clarity of illustration) to provide electrical energy the components of each of the devices 100, 190 and 200, as is known in the art. The power source 165 may be an electrochemical cell or a battery (primary or rechargeable), or the like, but may be any other suitable power source for providing electrical power to an implantable device which is known in the art.

In accordance with another preferred embodiment of the present invention a combined multi-modal cardio-therapeutic device may be constructed which will controllably use a combination of all the above disclosed therapeutic modalities and methods.

The general cardio-therapeutic device may be similar in construction to any of the devices 100, 150 and 190 of the present invention. However, the multi-modal cardio-therapy device may include software or suitable embedded program or programs which enable it to controllably and selectively apply any of the therapeutic modalities disclosed hereinabove based on the cardiac condition of the patient, but may also be programmed or controlled by a user such as a physician or cardiophysiologist to selectably disable or enable any of the cardiotherapy modalities available on the device.

For example, the implantable device 100 of FIG. 4 is capable of applying to the heart an anti-bradycardia pacing therapy mode, a plurality of anti-tachycardia therapy modes, including but not limited to cardioversion therapy modes, ATP modes, defibrillating shock therapy, and CCM signal anti-arrhythmic therapy mode. In addition to these anti-arrhythmic therapy modalities, the device 100 may also apply to the heart a cardiac contractility modulating therapy which is non-related to rhythm disturbances but is directed to modulate the contractility of the myocardium to achieve modulation of the cardiac output without modulating the heart rate. In a non-limiting example, the last modality may be used to increase the cardiac output of CHF patients by increasing the contractility of the left ventricle without substantially increasing the heart rate.

When the device 100 is operated in the full multi-modal capacity, the microprocessor unit 106 is operative to control and coordinate the operation and timing of the pacing unit 102, the anti-tachyarrhythmic unit 118, and the CCM unit 108, in accordance with the data received and processed by the microprocessor 106. Thus, the device 100 may provide coordinated multi modal therapies to the heart. The device 100 may apply CCM therapy to modulate the cardiac output when CCM therapy is indicated. The device 100 may also apply, simultaneously or separately, pacing therapy as is known in the art by controlling the pacing unit 102. The device 100 may apply anti-arrhythmic therapy to the heart based on the detection and classification methods disclosed hereinabove and known in the art implemented by using the output of the detecting unit 116.

The device 100 coordinates the application of the different therapy modalities such that, on one hand, the CCM signal induced artifacts do not interfere with the operation of arrhythmia detection and classification algorithms, as disclosed in detail hereinabove, and on the other hand, the CCM unit 108 may be utilized to deliver controlled anti-arrhythmic CCM therapy when an arrhythmia is detected as disclosed hereinabove. The device 100 also controls the anti-tachy-arrhythmic unit 118 to controllably and selectively apply tiered multi-modal therapy to the heart, including but not limited to, an ATP therapy mode, a cardioversion therapy mode and a defibrillation shock therapy mode, depending on the arrhythmia type detected by the classification algorithm operative on the microprocessor 106.

An aspect of the multi modal cardiotherapy devices of the present invention such as the exemplary device 100 is that while the device is capable of applying all the therapy modes available in a coordinated fashion based on the methods disclosed hereinabove, one or more of the therapy modes may be selectively disabled or switched off by suitable programming of the device 100. For example, the device 100 may be programmed to stop the delivery of cardiac output modulating therapy for the purpose of modulating the cardiac output, while still enabling the application of CCM signal delivery initiated as antiarrhythmic therapy following the detection of an arrhythmia. Similarly, the pacing therapy may be disabled while all the other therapy modalities are left operative. Other combinations of selective disabling of specific therapy modalities may also be possible. Such selective modality control may be advantageous since they may help in conserving battery power when one or more of the therapy modalities is not requested due to a change in the patient's cardiac conditions or to any other reason, while being fully reversible if the cardiac situation changes again.

The advantage of such a multi modal device, whether it is an external device or an implantable internal device, is that it provides the wide variety of possible cardiac modalities as disclosed hereinabove in one device, enables their use in the patient in a coordinated and controlled manner, and particularly in implantable versions of the device, obviates the need to implant multiple implantable cardiotherapy devices in the patient, such as for example, the implantation of a separate implantable cardiovertion/defibrillation device and a separate CCM device within the same patient which anyhow may be very difficult or even impossible to operate simultaneously in one patient due to the CCM induced artifact problem disclosed hereinabove.

It will be appreciated that the preferred embodiments disclosed hereinabove and illustrated in the drawings are given by way of example only and that many variations and modifications of the present invention may be made which are within the scope and spirit of the present invention.

What is claimed is:

1. A method for operating a multi-modal cardiotherapy device to deliver multi-modal cardiotherapy to a heart, the method comprising the steps of:
providing a device configured for delivering cardiac contractility modulating signals and a plurality of anti-arrhythmic therapy modalities to said heart;
applying cardiac contractility modulating signals to said heart to modulate the contractility of at least a portion of said heart;
detecting an arrhythmia or indications of possible arrhythmia in said heart;
delivering to said heart an anti-arrhythmic therapy selected from said plurality of anti-arrhythmic therapy modalities based on the type of said arrhythmia or said indications detected in said step of detecting; and
coordinating the application of cardiac contractility modulating signals of said step of applying with the delivering of said anti-arrhythmic therapy of said step of delivering.

2. The method according to claim 1 wherein said plurality of anti-arrhythmic therapy modalities comprises cardiac contractility modulating signal anti-arrhythmic therapy and one or more anti-arrhythmic therapy modalities selected from defibrillating shock therapy, cardioverting shock therapy, anti-tachycardia pacing therapy, variable energy shock therapy, anti-bradycardia pacing therapy and any combination thereof.

3. The method according to claim 2 wherein said cardiac contractility modulating signal anti-arrhythmic therapy comprises delivering one or more of said cardiac contractility modulating signals to said heart for reducing the prevalence of arrhythmic episodes detected in said heart.

4. The method according to claim 1 wherein said step of applying cardiac contractility modulating signals to said heart is performed for modulating the cardiac output of said heart.

5. The method according to claim 1 wherein said step of coordinating comprises the step of terminating the applying of cardiac contractility modulating signals to said heart of said step of applying, prior to or upon said delivering to said heart of said anti-arrhythmic therapy.

6. The method according to claim 5 wherein said step of coordinating comprises the step of renewing the applying of cardiac contractility modulating signals to said heart after said delivering to said heart of said anti-arrhythmic therapy is terminated.

7. The method according to claim 1 wherein said indications of possible arrhythmia include the detection of T-wave alternans in said heart.

8. The method according to claim 1 wherein said step of detecting further includes the step of determining the heart rate of said heart and disabling the applying of said cardiac contractility modulating signals to said heart within the duration of a cardiac contractility modulating signal free time period if said heart rate is larger than a first threshold value.

9. The method according to claim 1 wherein said step of detecting further includes the step of enabling the applying of said cardiac contractility modulating signals to said heart if no arrhythmia or indications of possible arrhythmia are detected within the duration of said cardiac contractility modulating signal free time period.

10. A method for operating a multi-modal cardiotherapy device to deliver multi-modal cardiotherapy to a heart, the device is configured for delivering cardiac contractility modulating signals and a plurality of anti-arrhythmic therapy modalities to said heart, the method comprising the steps of:
applying cardiac contractility modulating signals to said heart to modulate the cardiac output of said heart;
detecting an arrhythmia or indications of possible arrhythmia in said heart;
delivering to said heart an anti-arrhythmic therapy selected from said plurality of anti-arrhythmic therapy modalities based on the type of said arrhythmia or said indications detected in said step of detecting; and
coordinating the application of cardiac contractility modulating signals of said step of applying with the delivering of said anti-arrhythmic therapy of said step of delivering.

11. The method according to claim 10 wherein said plurality of anti-arrhythmic therapy modalities comprises cardiac contractility modulating signal anti-arrhythmic therapy and one or more anti-arrhythmic therapy modalities selected from defibrillating shock therapy, cardioverting shock therapy, anti-tachycardia pacing therapy, variable energy shock therapy, anti-bradycardia pacing therapy and any combination thereof.

12. The method according to claim 11 wherein said cardiac contractility modulating signal antiarrhythmic therapy comprises delivering one or more of said cardiac contractility modulating signals to said heart for reducing the prevalence of arrhythmic episodes detected in said heart.

13. The method according to claim 10 wherein said step of applying cardiac contractility modulating signals to said heart is performed for modulating the cardiac output of said heart.

14. The method according to claim 10 wherein said step of coordinating comprises the step of terminating the applying of cardiac contractility modulating signals to said heart of said step of applying, prior to or upon said delivering to said heart of said anti-arrhythmic therapy.

15. The method according to claim 14 wherein said step of coordinating comprises the step of renewing the applying of cardiac contractility modulating signals to said heart after said delivering to said heart of said anti-arrhythmic therapy is terminated.

16. The method according to claim 10 wherein said indications of possible arrhythmia include the detection of T-wave alternans in said heart, as an indication of a possible cardiac arrhythmia.

17. The method according to claim 10 wherein said step of detecting further includes the step of determining the heart rate of said heart and disabling the applying of said cardiac contractility modulating signals to said heart within the duration of a cardiac contractility modulating signal free time period if said heart rate is larger than a first threshold value.

18. The method according to claim 10 wherein said step of detecting further includes the step of enabling the applying of said cardiac contractility modulating signals to said heart if no arrhythmia or indications of possible arrhythmia are detected within the duration of said cardiac contractility modulating signal free time period.

19. A multi-modal cardiotherapy device comprising:
an anti-arrhythmic unit for delivering anti-arrhythmic therapy to said heart;
a cardiac contractility modulating unit configured for delivering cardiac contractility modulating signals to said heart for modulating the cardiac contractility of at least a portion of said heart, and for applying anti-arrhythmic cardiac contractility modulating signal therapy to said heart;

a sensing unit for sensing electrical signals related to electrical activity of said heart to provide an output signal;

a detecting unit operatively connected to said sensing unit for receiving said output signal of said sensing unit and for detecting in said output signal cardiac events of said heart;

a controller unit operatively connected to said anti-arrhythmic unit, said cardiac contractility modulating unit and said detecting unit; for processing the output of said detecting unit to detect a cardiac arrhythmia or indications of possible arrhythmia, controlling the application of said anti-arrhythmic therapy by said anti-arrhythmic unit, and for controlling the application of said anti-arrhythmic cardiac contractility modulating signal therapy, and the modulating of said cardiac contractility of said portion of said heart by said cardiac contractility modulating unit; and at least one power source for providing power to said anti-arrhythmic therapy unit, said cardiac contractility modulating unit, said sensing unit, said detecting unit, and said controller unit.

20. The multi-modal cardiotherapy device according to claim 19, wherein said anti-arrhythmic unit is configured for delivering to said heart multiple modes of ant-arrhythmic therapy selected from anti-bradycardia pacing therapy, defibrillating shock therapy, cardioverting shock therapy, anti-tachycardia pacing therapy, variable energy shock therapy, and any combination thereof.

21. The multi-modal cardiotherapy device according to claim 19, wherein said controller unit is configured for coordinating the application to said heart of anti-arrhythmic therapy by said anti-arrhythmic unit with the application to said heart of said anti-arrhythmic cardiac contractility modulating signal therapy by said cardiac contractility modulating unit.

22. The multi-modal cardiotherapy device according to claim 19, wherein said controller unit is configured for coordinating the application to said heart of anti-arrhythmic therapy by said anti-arrhythmic unit with said modulating of said cardiac contractility by said cardiac contractility modulating unit.

23. The multi-modal cardiotherapy device according to claim 19, wherein said anti-arrhythmic unit comprises a pacing unit configured for pacing at least one chamber of said heart.

24. The multi-modal cardiotherapy device according to claim 19 wherein said cardiac contractility modulating unit is configured for controllably delivering cardiac contractility modulating signal anti-arrhythmic therapy to said heart by controllably delivering one or more of said cardiac contractility modulating signals to said heart for reducing the prevalence of arrhythmic episodes detected in said heart.

25. The multi-modal cardiotherapy device according to claim 19 wherein said cardiac contractility modulating unit is configured for modulating the cardiac output of said heart by delivering said cardiac contractility modulating signals to said heart.

26. The multi-modal cardiotherapy device according to claim 19 wherein said controller unit is configured for terminating the applying of cardiac contractility modulating signals to said heart prior to or upon said delivering to said heart of said anti-arrhythmic therapy.

27. The multi-modal cardiotherapy device according to claim 19 wherein said controller unit is configured for renewing the applying of cardiac contractility modulating signals to said heart after said delivering to said heart of said anti-arrhythmic therapy is terminated.

28. The multi-modal cardiotherapy device according to claim 19 wherein said detecting unit is configured for detecting T-wave alternans in said heart, as an indication of a possible cardiac arrhythmia.

29. The multi-modal cardiotherapy device according to claim 19 further including electrodes operatively connected to said anti-arrhythmic unit, said cardiac contractility modulating unit, and said sensing unit, for delivering said anti-arrhythmic therapy to said heart, for applying said cardiac contractility modulating signals to said heart, and for sensing said electrical signals, respectively.

30. The multi-modal cardiotherapy device according to claim 19 wherein said controller unit is configured for determining the heart rate of said heart and for disabling said modulating of said cardiac contractility of said portion of said heart by said cardiac contractility modulating unit within the duration of a cardiac contractility modulating signal free time period if said heart rate is larger than a first threshold value.

31. The multi-modal cardiotherapy device according to claim 19 wherein said controller unit is configured for enabling said modulating of said cardiac contractility of said portion of said heart by said cardiac contractility modulating unit if no arrhythmia or indications of possible arrhythmia are detected within the duration of said cardiac contractility modulating signal free time period.

32. A multi-modal cardiotherapy device comprising:

anti-arrhythmic means for delivering multiple modes of anti-arrhythmic therapy to said heart;

cardiac contractility modulating means configured for delivering cardiac contractility modulating signals to said heart, for modulating the cardiac contractility of at least a portion of said heart, and for applying anti-arrhythmic cardiac contractility modulating signal therapy to said heart;

sensing means for sensing electrical signals related to cardiac activity sensed at said heart;

detecting means operatively connected to said sensing means for receiving the output signal of said sensing means and for detecting cardiac depolarization events of said heart;

controller means operatively connected to said anti-arrhythmic means, said cardiac contractility modulating means and said detecting means, for processing the output of said detecting means to detect a cardiac arrhythmia or indications of possible arrhythmia, controlling the application of said anti-arrhythmic therapy modes by said anti-arrhythmic means, and for controlling the application of said anti-arrhythmic cardiac contractility modulating signal therapy, and the modulating of said cardiac contractility by said cardiac contractility modulating means; and means for providing power to said anti-arrhythmic means, said cardiac contractility modulating means, said sensing means, said detecting means and said controller means.

33. The multi-modal cardiotherapy device according to claim 32, wherein said anti-arrhythmic means is configured for delivering to said heart multiple modes of anti-arrhythmic therapy selected from anti-bradycardia pacing therapy, defibrillating shock therapy, cardioverting shock therapy, anti-tachycardia pacing therapy, variable energy shock therapy, and any combination thereof.

34. The multi-modal cardiotherapy device according to claim 32, wherein said controller means is configured for coordinating the application to said heart of anti-arrhythmic therapy by said anti-arrhythmic means with the application to said heart of said anti-arrhythmic cardiac contractility modulating signal therapy by said cardiac contractility modulating means.

35. The multi-modal cardiotherapy device according to claim 32, wherein said controller means is configured for coordinating the application to said heart of anti-arrhythmic therapy by said anti-arrhythmic means with said modulating of said cardiac contractility by said cardiac contractility modulating means.

36. The multi-modal cardiotherapy device according to claim 32, wherein said anti-arrhythmic means comprises pacing means configured for pacing at least one chamber of said heart.

37. The multi-modal cardiotherapy device according to claim 32 wherein said cardiac contractility modulating means is configured for controllably delivering cardiac contractility modulating signal anti-arrhythmic therapy to said heart by controllably delivering one or more of said cardiac contractility modulating signals to said heart for reducing the prevalence of arrhythmic episodes detected in said heart.

38. The multi-modal cardiotherapy device according to claim 32 wherein said cardiac contractility modulating means is configured for modulating the cardiac output of said heart by delivering said cardiac contractility modulating signals to said heart.

39. The multi-modal cardiotherapy device according to claim 32 wherein said controller means is configured for terminating the applying of cardiac contractility modulating signals to said heart prior to or upon said delivering to said heart of said anti-arrhythmic therapy.

40. The multi-modal cardiotherapy device according to claim 32 wherein said controller means is configured for renewing the applying of cardiac contractility modulating signals to said heart after said delivering to said heart of said anti-arrhythmic therapy is terminated.

41. The multi-modal cardiotherapy device according to claim 32 wherein said detecting means is configured for detecting T-wave alternans in said heart, as an indication of a possible cardiac arrhythmia.

42. The multi-modal cardiotherapy device according to claim 32 further including electrode means operatively connected to said anti-arrhythmic means, said cardiac contractility modulating means and said sensing means, for delivering said anti-arrhythmic therapy to said heart, for applying said cardiac contractility modulating signals to said heart, and for sensing said electrical signals, respectively.

43. The multi-modal cardiotherapy device according to claim 32 wherein said controller means is configured for determining the heart rate of said heart and for disabling said modulating of said cardiac contractility of said portion of said heart by said cardiac contractility modulating means within the duration of a cardiac contractility modulating signal free time period if said heart rate is larger than a first threshold value.

44. The multi-modal cardiotherapy device according to claim 32 wherein said controller means is configured for enabling said modulating of said cardiac contractility of said portion of said heart by said cardiac contractility modulating means if no arrhythmia or indications of possible arrhythmia are detected within the duration of said cardiac contractility modulating signal free time period.

\* \* \* \* \*